(12) United States Patent
Ignatyev et al.

(10) Patent No.: US 9,056,881 B2
(45) Date of Patent: Jun. 16, 2015

(54) PROCESS FOR THE PREPARATION OF PHOSPHINIC ACID ESTERS

(71) Applicant: Merck Patent GmbH, Darmstadt (DE)

(72) Inventors: Nikolai Mykola Ignatyev, Duisburg (DE); Michael Schulte, Bischofsheim (DE); Christoph Alexander Jablonka, Duesseldorf (DE); Karsten Koppe, Marl-Polsum (DE); Walter Frank, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/382,344

(22) PCT Filed: Feb. 12, 2013

(86) PCT No.: PCT/EP2013/000408
§ 371 (c)(1),
(2) Date: Sep. 2, 2014

(87) PCT Pub. No.: WO2013/127493
PCT Pub. Date: Sep. 6, 2013

(65) Prior Publication Data
US 2015/0045572 A1    Feb. 12, 2015

(30) Foreign Application Priority Data
Mar. 2, 2012 (DE) .......... 10 2012 004 068

(51) Int. Cl.
C07F 9/32     (2006.01)
C07F 9/6571   (2006.01)

(52) U.S. Cl.
CPC ............ *C07F 9/3205* (2013.01); *C07F 9/327* (2013.01); *C07F 9/657163* (2013.01)

(58) Field of Classification Search
USPC .................................. 558/83, 114; 568/16
See application file for complete search history.

(56) References Cited

U.S. PATENT DOCUMENTS

| 7,576,242 B2 | 8/2009 | Ignatyev et al. |
| 2007/0128515 A1 | 6/2007 | Ignatyev et al. |

FOREIGN PATENT DOCUMENTS

WO   2005/049555 A1   6/2005

OTHER PUBLICATIONS

International Search Report dated Jun. 5, 2013 issued in corresponding PCT/EP20131000408 application (pp. 1-2).
V. Ya. Semenii et al., "Mechanism of Intermolecular Interactions in Complexes of Tris (Perfluoroalkyl) Phosphine Oxides with Aliphatic Alcohols", Institute of Organic Chemistry, vol. 48, No. 6 (Jun. 1978) pp. 1213-1218.
N.V. Pavlenko et al., "Esters of Bis (Perfluoroalkyl) Phosphinic Acids", Institute of Organic Chemistry, vol. 59, No. 3 (Mar. 1989) pp. 474-476.

*Primary Examiner* — Kristin Vajda
(74) *Attorney, Agent, or Firm* — Millen, White, Zelano & Branigan P.C.

(57) ABSTRACT

The invention relates to a process for the preparation of alkyl phosphinates, alkenyl phosphinates, alkynyl phosphinates or phenyl phosphinates by reaction of a corresponding phosphine oxide with an alcohol or phenol in the presence of alkali-metal fluoride or tetraalkylammonium fluoride.

7 Claims, No Drawings

PROCESS FOR THE PREPARATION OF PHOSPHINIC ACID ESTERS

The invention relates to a process for the preparation of alkyl phosphinates, alkenyl phosphinates, alkynyl phosphinates or phenyl phosphinates by reaction of a corresponding phosphine oxide with an alcohol or phenol in the presence of alkali-metal fluoride or tetraalkylammonium fluoride.

Alkyl esters of bis(alkyl)phosphinic acids are known flameproofing agents and assistants for the reduction of viscosities. The alkylating power of the alkyl bis(alkyl)phosphinates can be increased by exchange of the alkyl group by partially fluorinated alkyl groups or perfluorinated alkyl group. The methyl ester of bis(heptafluoropropyl)phosphinic acid is, according to N. V. Pavlenko et al, J. Gen. Chem. USSR (Engl. Transl.), 59, 3, 1989, 474-476, capable of methylating the weak base 2-trifluoromethylbenzothiazole quantitatively at 20° C.

The methyl ester of bis(pentafluoroethyl)phosphinic acid is, according to N. V. Ignat'ev, J. Fluorine Chem., 130, 2009, 1183-1191, capable of methylating the chloride or bromide of an organic salt with chloride or bromide anion. Organic salts with bis(pentafluoroethyl)phosphinate anions also form in this alkylation reaction.

The methyl ester of bis(trifluoromethyl)phosphinic acid can be prepared, for example, by alkylation of mercury bis(trifluoromethyl)phosphinate using methyl iodide (A. B. Burg et al, Inorg. Chem., 8, 5, 1969, 1199-1201). Alkyl esters of bis(heptafluoropropyl)phosphinic acid can be prepared, for example, by reaction of silver bis(heptafluoropropyl)phosphinate with alkyl iodides (N. V. Pavlenko et al, J. Gen. Chem. USSR (Engl. Transl), 59, 3, 1989, 474-476).

Alkyl esters of bis(perfluoroalkyl)phosphinic acids can also be prepared by alcoholysis of bis(perfluoroalkyl)phosphinyl chlorides in the presence of an organic base, for example in the presence of trimethylamine (R. G. Cavell et al, Inorg. Chem., 18, 10, 1979, 2901-2908). However, the alcoholysis does not succeed in satisfactory yield with methanol.

Even without the presence of base, the methanolysis of bis(perfluoroalkyl)-phosphinyl chloride is not satisfactory. N. V. Pavlenko et al, J. Gen. Chem. USSR (Engl. Transl), 59, 3, 1989, 474-476 postulates that the methyl ester formed as an intermediate reacts with methanol to form the dimethyl ether, and bis(perfluoroalkyl)phosphinic acid forms.

Alkyl esters of bis(perfluoroalkyl)phosphinic acids can also be prepared by reaction of perfluoroalkyl iodides with alkyl phosphates, (alkylO)$_3$P=O, at temperatures of 60° C. in the presence of zinc/copper and subsequent acidic hydrolysis (S. Benefice-Malouet et al, J. Fluorine Chem., 30, 1985, 171-188).

Patent US 2003-189193 describes a process for the preparation of methyl esters of bis(perfluoroalkyl)phosphinic acids by conversion of perfluoroalkyl iodides into Grignard reagents (R$_F$MgBr) at temperatures below −45° C. and reaction thereof with POCl$_3$ and subsequent reaction with methanol.

There is still a need to prepare this interesting class of alkylating agents in an alternative way to conventional methods.

The object of the invention is therefore to develop an alternative or improved process for the preparation of alkyl esters of phosphinic acids which meets the demands of an industrial-scale economical synthesis.

It is known to date that tris(perfluoroalkyl)phosphine oxides form complexes with alcohols (V. Ya. Semenii et al, Zh. Obshchei Khim. (Russ), 48, 6, 1978, 1325-1331). Complexes of this type decompose on warming above 40° C. and form various decomposition products. Isolation of alkyl esters of a bis(perfluoroalkyl)phosphinic acid is not described. Rapid reaction of the alkyl esters in the presence of alcohol with formation of bis(perfluoroalkyl)-phosphinic acid is also assumed here.

A similar result has also been observed by N. V. Pavlenko et al, J. Gen. Chem. USSR (Engl. Transl.), 59, 3, 1989, 474-476. In the case of the reaction of bis(heptafluoropropyl)phosphine oxide with methanol, only bis(heptafluoropropyl)phosphinic acid and dimethyl ether were isolated.

Surprisingly, it has been found that the addition of an alkali-metal fluoride or tetraalkylammonium fluoride enables isolation of the desired alkyl esters, which were hitherto merely postulated as intermediates. The alkyl groups of the tetraalkylammonium fluoride are in each case, independently of one another, a straight-chain or branched alkyl group having 1 to 10 C atoms.

Accordingly, the invention relates firstly to a process for the preparation of phosphinic acid esters of the formula (I)

$$(C_nF_{2n+1-y}H_y)_2P(O)OR \qquad (I),$$ 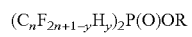

where n in each case, independently of one another, denotes 1, 2, 3, 4, 5, 6, 7, 8, 9, 10, 11 or 12, y in each case, independently of one another, denotes 0, 1, 2, 3 or 4, R denotes unsubstituted or substituted phenyl, a straight-chain or branched, unfluorinated or partially fluorinated or deuterated alkyl group having 1 to 30 C atoms or a straight-chain or branched, unfluorinated or partially fluorinated alkenyl or alkynyl group having 3 to 30 C atoms, where R may be partially substituted by halogen and/or partially substituted by —OH, —C(O)OH, N(CH$_3$)$_2$ and —CN and where one or two carbon atoms of the alkyl, alkenyl or alkynyl group which are not adjacent and are not in the α-position to the oxygen atom or to carbon atoms of the double bond or triple bond may be replaced by atoms and/or atom groups selected from the group —O—, —S—, —S(O)—, —SO$_2$—, —C(O)—, —C(O)O— or —N(R')— and R' in each case, independently of one another, denotes H, a straight-chain or branched, unfluorinated or partially fluorinated alkyl group having 1 to 18 C atoms, saturated C$_3$- to C$_7$-cycloalkyl, unsubstituted or substituted phenyl, by reaction of a phosphine oxide of the formula (II)

$$(C_nF_{2n+1-y}H_y)_3P(O) \qquad (II),$$ 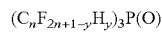

where n and y have a meanings indicated in the case of the formula (I), with an alcohol or phenol R—OH in the presence of alkali-metal fluoride or tetraalkylammonium fluoride, where R has a meaning indicated in the case of the formula (I), where the water content in this reaction is in total a maximum of 1000 ppm and where alkyl in tetraalkylammonium in each case, independently of one another, denotes a straight-chain or branched alkyl group having 1 to 10 C atoms.

The starting compounds, i.e. the phosphine oxides of the formula (II), alcohols or phenols ROH, alkali-metal fluorides and/or tetraalkylammonium fluorides named, are commercially available or can be prepared by known methods.

The phosphine oxides of the formula (II) can be prepared, for example, by reaction of tris(fluoroalkyl)difluorophosphoranes or tris(perfluoroalkyl)-difluorophosphoranes with alkaline-earth metal oxides, alkaline-earth metal carbonates, zinc oxide, copper(I) oxide, copper(II) oxide, silver oxide, mercury(II) oxide, cadmium oxide or cadmium carbonate, as described in WO 2011/110281. The preparation of the starting compounds tris(perfluoroalkyl)difluorophosphorane can be prepared, for example, by electrochemical fluorination of suitable starting compounds, as described in V. Ya. Semenii et al, Zh. Obshch. Khim., 55, 12, 1985, 2716-2720, N. Ignatiev et al, J. of Fluorine Chem., 103, 2000, 57-61 and WO 00/21969. The corresponding descriptions are hereby incorporated by way of reference and are regarded as part of the disclosure.

The reaction according to the invention is particularly preferably carried out with exclusion of water, where the water content is in total a maximum of 1000 ppm. The water content is very particularly preferably in total 10 to 200 ppm.

The alcohol or phenol ROH is preferably employed with a residual water content between 10 to 1000 ppm, particularly preferably with a residual water content between 10 and 200 ppm.

The alkali-metal fluoride or tetraalkylammonium fluoride is preferably employed with a residual water content between 0 to 990 ppm, particularly preferably with a residual water content between 0 and 190 ppm.

In accordance with the invention, the alkali-metal fluorides from the group lithium fluoride, sodium fluoride, potassium fluoride, rubidium fluoride or caesium fluoride can be employed or tetraalkylammonium fluorides in which the alkyl group in each case, independently of one another, denotes a straight-chain or linear alkyl group having 1 to 10 C atoms.

A straight-chain or branched alkyl group having 1 to 10 C atoms is, for example, methyl, ethyl, isopropyl, propyl, butyl, sec-butyl or tert-butyl, pentyl, 1-, 2- or 3-methylbutyl, 1,1-, 1,2- or 2,2-dimethylpropyl, 1-ethyl-propyl, n-hexyl, n-heptyl, n-octyl, n-nonyl or n-decyl.

Preferred tetraalkylammonium fluorides are salts in which all alkyl groups are identical, for example tetramethylammonium fluoride or tetra(n-butyl)-ammonium fluoride.

In accordance with the invention, the fluorides potassium fluoride, sodium fluoride, rubidium fluoride, caesium fluoride or tetramethylammonium fluoride are preferably employed. Potassium fluoride is very particularly preferably employed.

The amount of the above-described alkali-metal fluoride or tetraalkylammonium fluoride employed is preferably between 0.05 and 0.5 mol based on 1 mol of phosphine oxide of the formula (II), very particularly preferably 0.1 mol based on 1 mol of phosphine oxide of the formula (II).

The solids employed in the process according to the invention should preferably be employed in the ground (spray-dried) state in order that the largest possible surface area is present for the reaction.

Any type of grinding is possible, for example grinding by means of a ball mill.

In the process according to the invention, the alcohol or phenol ROH can, as described above or below, be employed with an excess up to 10%, compared with the amount of the phosphine oxide of the formula (II) employed, as described in detail above or below. The two compounds are preferably employed in equimolar amount.

In a preferred embodiment of the process, the alkali-metal fluoride or tetraalkylammonium fluoride is added to the phosphine oxide of the formula (II) at temperatures of −10° C. to 0° C., the alcohol or phenol is added, and the reaction mixture is subsequently warmed to a temperature of 20° C. to 60° C. until the reaction is complete.

In a particularly preferred embodiment of the process, the alkali-metal fluoride or tetraalkylammonium fluoride is added to the phosphine oxide of the formula (II) at 0° C., the mixture is optionally stirred at this temperature for one hour, the alcohol or phenol is then added, and the reaction mixture is warmed at a temperature of 25° C. until the reaction is complete.

The reaction can be carried out in a glass apparatus or in an apparatus made from plastic (such as, for example, Teflon) or steel.

Working without solvents is preferred. However, it is also possible to work in the presence of solvents which are inert to the compounds of the formula (I) and (II) and to alkali-metal fluorides or tetraalkylammonium fluorides, for example acetonitrile, propionitrile, hexane or 1,2-dimethoxyethane.

Preference is given to the preparation of compounds of the formula (I), as described above, in which the variable y denotes 0, 1 or 2, particularly preferably in which the variable y denotes 0.

Accordingly, preference is given to starting materials of the formula (II) in which the variable y denotes 0, 1 or 2, particularly preferably the starting materials of the formula (II) are preferred in which the variable y denotes 0.

Preference is given to the preparation of compounds of the formula (I), as described above, in which the variable n denotes 1, 2, 3 or 4, particularly preferably in which the variable n denotes 2, 3 or 4.

In the compounds of the formula (I) or in the alcohol or phenol ROH, R denotes unsubstituted or substituted phenyl, a straight-chain or branched, unfluorinated or partially fluorinated or deuterated alkyl group having 1 to 30 C atoms or a straight-chain or branched, unfluorinated or partially fluorinated alkenyl or alkynyl group having 3 to 30 C atoms, where R may be partially substituted by halogen and/or partially substituted by —OH, —C(O)OH, N(CH$_3$)$_2$ and —CN and where one or two carbon atoms of the alkyl, alkenyl or alkynyl group which are not adjacent and are not in the α-position to the oxygen atom or to carbon atoms of the double bond or triple bond may be replaced by atoms and/or atom groups selected from the group —O—, —S—, —S(O)—, —SO$_2$—, —C(O)—, —C(O)O— or —N(R')— and R' in each case, independently of one another, denotes H, a straight-chain or branched, unfluorinated or partially fluorinated alkyl group having 1 to 18 C atoms, saturated C$_3$- to C$_7$-cycloalkyl, unsubstituted or substituted phenyl.

A straight-chain or branched alkyl group having 1 to 30 C atoms encompasses the group described above of straight-chain or branched alkyl group having 1 to 10 C atoms and undecanyl, dodecanyl, tridecanyl, tetradecanyl, pentadecanyl, hexadecanyl, heptadecanyl, octadecanyl, nonadecanyl, eicosanyl, heneicosanyl, docosanyl, tricosanyl, tetracosanyl, pentacosanyl, hexacosanyl, heptacosanyl, octacosanyl, nonacosanyl and triacontanyl.

A straight-chain or branched alkenyl or alkynyl having 3 to 30 C atoms, where a plurality of double or triple bonds may also be present, is, for example, allyl, 2- or 3-butenyl, isobutenyl, sec-butenyl, furthermore 4-pentenyl, isopentenyl, hexenyl, heptenyl, octenyl, —C$_9$H$_{17}$, —C$_{10}$H$_{19}$ to —C$_{30}$H$_{49}$, propargyl, 2- or 3-butynyl, C$_5$H$_7$ to C$_{30}$H$_{47}$, preferably allyl, 2- or 3-butenyl, isobutenyl, sec-butenyl, 4-pentenyl, isopentenyl, hexenyl or decenyl or propargyl.

Partially fluorinated means that at least one H atom of the corresponding alkyl, alkenyl or alkynyl group has been replaced by an F atom. Perfluorinated means that all H atoms of the corresponding alkyl or alkenyl or alkynyl group have been replaced by F atoms. Deuterated means that at least one H atom of the corresponding alkyl, alkenyl or alkynyl group has been replaced by a deuterium atom.

Examples of a straight-chain or branched alkyl group having 2 to 10 C atoms, which may be partially substituted by halogen and/or partially substituted by —OH, —C(O)OH, N(CH$_3$)$_2$ and —CN and where one or two carbon atoms which are not adjacent and are not in the α-position to the oxygen atom or to carbon atoms of the double bond or triple bond may be replaced by atoms and/or atom groups selected from the group —O—, —S—, —S(O)—, —SO$_2$—, —C(O)—, —C(O)O— or —N(R')—, are —CH$_2$—O—CH$_3$, —CH$_2$—CH$_2$—O—CH$_3$, —CH$_2$—CH$_2$—O—CH$_2$—CH$_3$, —CH$_2$—C(O)OH, —CH$_2$—CH$_2$—NH—CH$_3$, —CH$_2$—N(CH$_3$)$_2$, —CH$_2$—CH$_2$—N(CH$_3$)$_2$, —CH$_2$—S—CH$_3$, —CH$_2$—CH$_2$—S—CH$_3$, —CH$_2$—CH$_2$—S—CH$_2$—CH$_3$, —CH$_2$—CH$_2$—S(O)$_2$OH, —CH$_2$—CH$_2$—CH$_2$—S(O)$_2$OH, —CH$_2$—CH$_2$—CH$_2$—CH$_2$—S(O)$_2$OH, —CH$_2$—CH$_2$—O—CH$_2$—CH$_2$—O—CH$_3$, —CH$_2$—CH$_2$—O—CH$_2$—CH$_2$—S—CH$_3$, —CH$_2$—CH$_2$—O—CH$_2$—CH$_2$—O—CH$_2$—CH$_2$—O—CH$_3$, —CH$_2$—CH$_2$—S(O)—CH$_3$, —CH$_2$—CH$_2$—SO$_2$—CH$_3$, —CH$_2$—CH$_2$—C(O)—CH$_3$, —CH$_2$—CH$_2$—C(O)O—CH$_3$, —CH(CH$_3$)—C(O)OH, —CH$_2$—CH$_2$—CH$_2$—C(O)OH, —(CH$_2$)$_9$—C(O)O—CH$_3$, —CH$_2$—CH$_2$—O—CH$_2$—CH$_2$—O—CH$_2$—CH$_2$—C(O)O—CH$_2$—CH$_2$—CH$_3$, —CH$_2$—CH$_2$—CH$_2$—Br, —CH$_2$—CH$_2$—O—CH$_2$CF$_3$, —CH$_2$—CH$_2$—CH$_2$—OH or —CH$_2$—CH$_2$—CN.

Examples of a straight-chain or branched partially fluorinated alkyl group having 3 to 10 C atoms, where one or two carbon atoms which are not adjacent and are not in the α-position to the oxygen atom may be replaced by atoms and/or atom groups selected from the group —O—, —S—, —S(O)—, —SO$_2$—, —C(O)—, —C(O)O— or —N(R')—, are —CH$_2$—CH$_2$—O—CF$_3$, —CH$_2$—CH$_2$—O—CH$_2$—CF$_3$, —CH$_2$—(CF$_2$)$_3$—CF$_2$H, —CH$_2$—CH$_2$—N(CF$_3$)$_2$, —CH$_2$—CH$_2$—S—CF$_3$, —CH$_2$—CH$_2$—S—CH$_2$—CF$_3$, —CH$_2$—CH$_2$—O—CF$_2$—CF$_2$—O—CH$_3$, —CH$_2$—CH$_2$—S(O)—CF$_3$, —CH$_2$—CH$_2$—SO$_2$—CF$_3$, —CH$_2$—CH$_2$—C(O)—CH$_2$—CF$_3$, —CH$_2$—CH$_2$—C(O)O—CH$_2$—CF$_3$ or —CH$_2$—CH$_2$—(CF$_2$)$_2$—C(O)O—CH$_3$.

Examples of a straight-chain or branched alkenyl group having 3 to 10 C atoms, where one or two carbon atoms which are not adjacent and are not in the α-position to the oxygen atom may be replaced by atoms and/or atom groups selected from the group —O—, —S—, —S(O)—, —SO$_2$—, —C(O)—, —C(O)O— or —N(R')—, are —CH$_2$—O—CH=CH$_2$, —CH$_2$—S—CH=CH$_2$, —CH$_2$—NH—CH=CH$_2$, —CH$_2$—N(CH$_3$)—CH$_2$—CH=CH$_2$, —CH$_2$—CH$_2$—O—CH$_2$—CH=CH$_2$, —CH$_2$—CH$_2$—O—CH=CH$_2$, —CH$_2$—CH$_2$—S—CH$_2$—CH=CH$_2$, —CH$_2$—CH$_2$—C(O)—CH$_2$—CH=CH$_2$, —CH$_2$—CH$_2$—C(O)—CH=CH$_2$, —CH$_2$—CH$_2$—C(O)O—CH$_2$—CH=CH$_2$, —CH$_2$—CH$_2$—S(O)—CH$_2$—CH=CH$_2$, —CH$_2$—CH$_2$—SO$_2$—CH$_2$—CH=CH$_2$, —CH$_2$—(CH$_2$)$_2$—O—CH$_2$—CH=CH$_2$, —CH$_2$—(CH$_2$)$_3$—O—CH$_2$—CH=CH$_2$, —CH$_2$—(CH$_2$)$_4$—O—CH$_2$—CH=CH$_2$, —CH$_2$—(CH$_2$)$_5$—O—CH$_2$—CH=CH$_2$ or —CH$_2$—(CH$_2$)$_6$—O—CH$_2$—CH=CH$_2$.

Examples of a straight-chain or branched alkynyl group having 3 to 10 C atoms, where one or two carbon atoms which are not adjacent and are not in the α-position to the oxygen atom may be replaced by atoms and/or atom groups selected from the group —O—, —S—, —S(O)—, —SO$_2$—, —C(O)—, —C(O)O— or —N(R')—, are —CH$_2$—N(CH$_3$)—CH$_2$—C≡CH, —CH$_2$—CH$_2$—O—CH$_2$—C≡CH, —CH$_2$—CH$_2$—S—CH$_2$—C≡CH, —CH$_2$—CH$_2$—C(O)—CH$_2$—C≡CH, —CH$_2$—CH$_2$—C(O)—C≡CH, —CH$_2$—CH$_2$—C(O)O—CH$_2$—C≡CH, —CH$_2$—CH$_2$—S(O)—CH$_2$—C≡CH, —CH$_2$—CH$_2$—SO$_2$—CH$_2$—C≡CH, —CH$_2$—(CH$_2$)$_2$—O—CH$_2$—C≡CH, —CH$_2$—(CH$_2$)$_3$—O—CH$_2$—C≡CH, —CH$_2$—(CH$_2$)$_4$—O—CH$_2$—C≡CH, —CH$_2$—(CH$_2$)$_5$—O—CH$_2$—C≡CH or —CH$_2$—(CH$_2$)$_6$—O—CH$_2$—C≡CH.

Examples of a saturated $C_3$- to $C_7$-cycloalkyl are cyclopropyl, cyclobutyl, cyclopentyl, cyclohexyl or cycloheptyl.

Substituted phenyl in R' or R denotes a phenyl group, which may be substituted by a straight-chain or branched, unfluorinated, partially fluorinated or perfluorinated alkyl group having 1 to 6 C atoms, a straight-chain or branched, unfluorinated, partially fluorinated or perfluorinated alkenyl group having 2 to 10 C atoms, a straight-chain or branched, unfluorinated, partially fluorinated or perfluorinated alkynyl group having 2 to 10 C atoms, —CN, —NO$_2$, F, Cl, Br, I, —OH, a straight-chain or branched, unfluorinated, partially fluorinated or perfluorinated alkoxy group having 1 to 6 C atoms, N(R")$_2$, —COOH, —C(O)OR", —C(O)R", —SO$_2$X', —SR", —S(O)R", —SO$_2$R", SO$_2$N(R")$_2$ or SO$_3$H, where X' denotes F, Cl or Br and R" denotes an unfluorinated, partially fluorinated or perfluorinated straight-chain or branched alkyl group having 1 to 6 C atoms, for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxy-phenyl, o-, m- or p-methoxyphenyl, o-, m- or p-ethoxyphenyl, o-, m- or p-(trifluoromethyl)phenyl, o-, m- or p-(trifluoromethoxy)phenyl, o-, m- or p-(trifluoromethylsulfonyl)phenyl, o-, m- or p-fluorophenyl, o-, m- or p-chloro-phenyl, o-, m- or p-bromophenyl, o-, m- or p-iodophenyl.

Preference is given to the preparation of compounds of the formula (I) in which R denotes a straight-chain or branched unfluorinated or partially fluorinated alkyl group having 1 to 10 C atoms, a straight-chain or branched alkenyl group having 3 to 10 C atoms, a straight-chain or branched alkynyl group having 3 to 10 C atoms or unsubstituted or substituted phenyl, where one or two carbon atoms which are not adjacent and are not in the α-position to the oxygen atom or to carbon atoms of the double bond or triple bond may be replaced by atoms and/or atom groups selected from the group —O—, —C(O)— or C(O)O—.

Particular preference is given to the preparation of compounds of the formula (I) in which R denotes a straight-chain or branched unfluorinated or partially fluorinated alkyl group having 1 to 4 C atoms, a straight-chain or branched alkenyl group having 3 to 10 C atoms, a straight-chain alkynyl group having 3 to 6 C atoms or phenyl, where a carbon atom which is not adjacent and is not in the α-position to the oxygen atom or to carbon atoms of the double bond or triple bond may be replaced by —O—.

Very particular preference is given to the preparation of compounds of the formula (I) in which R denotes methyl, ethyl, 2,2,2-trifluoroethoxyethyl, 3-bromopropyl, 3-hydroxypropyl, 2-cyanoethyl, 2,2,3,3,4,4,5,5-octafluoropentyl, allyloxyethyl, allyl, decenyl, propargyl or phenyl.

The compounds of the formula (I) prepared by the process according to the invention, as described above, are pure compounds and are ideally suitable for the further reaction, in particular for the alkylation of organic compounds, but in particular for the preparation of organic salts with the phosphinate anion corresponding to the phosphinic acid ester. The following examples also show, inter alia, this application.

The compounds of the formula (I) may also be prepared in deuterated form in accordance with the invention by starting from deuterated alcohols or phenols and reacting correspondingly to the process according to the invention.

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

NMR spectroscopy: NMR samples are measured either in a 5 mm ($Ø_A$) glass NMR tube or in a 3.7 mm ($Ø_A$) FEP inliner at 25° C. In the case of measurements in FEP, the inliner is introduced into a 5 mm ($\varnothing_A$) precision glass NMR tube (Wilmad 537). The locking agent (CD$_3$CN) is thus located in the glass NMR tube between glass and FEP inliner. The measurements are carried out on a 400 MHz Bruker Avance III spectrometer with a 9.3980 T cryomagnet and a 5 mm BBFO sample head.

$^1$H NMR spectra are measured in a $^1$H/$^{19}$F channel at 400.17 MHz. $^{13}$C, $^{19}$F and $^{31}$P NMR spectra were measured in a broadband channel at 100.62, 376.54 and 161.99 MHz. The $^1$H NMR chemical shifts are relative to tetramethylsilane (TMS) and arise for the solvents CDCl$_3$ (7.24 ppm) and CD$_3$CN (1.95 ppm). The $^{13}$C chemical shifts are likewise relative to TMS and arise for the solvents CDCl$_3$ (77.2 ppm) and CD$_3$CN (118.7 ppm). The $^{19}$F chemical shifts are relative to CFCl$_3$ and arise for the internal standards C$_6$F$_6$ (−162.9 ppm) or C$_6$H$_5$CF$_3$ (−63.9 ppm). The $^{31}$P chemical shifts are relative to H$_3$PO$_4$ (85%).

Example 1

Preparation of methyl bis(pentafluoroethyl)phosphinate, (C$_2$F$_5$)$_2$P(O)OCH$_3$, without alkali-metal or tetraalkylammonium fluoride

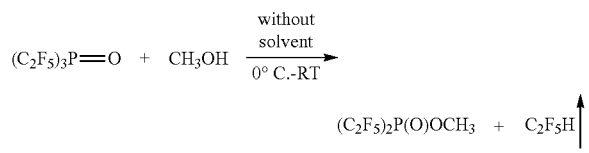

Dry methanol (0.697 g; 21.8 mmol) is added to cooled (0° C.) tris(pentafluoroethyl)phosphine oxide, (C$_2$F$_5$)$_3$P=O, (8.42 g; 20.8 mmol) in a 100 ml glass flask. A two-phase reaction mixture is observed. This is stirred at 0° C. for 1 h and subsequently at room temperature for 47 h. After about 20 minutes at room temperature, a clear and colourless reaction solution is observed. With increasing time at room temperature, the solution becomes a pale-yellow colour.

Composition in the $^{31}$P-NMR spectrum after 47 h at room temperature: methyl bis(pentafluoroethyl)phosphinate, (C$_2$F$_5$)$_2$P(O)OCH$_3$: 2% tris(pentafluoroethyl)phosphine oxide, (C$_2$F$_5$)$_3$P=O: 55% bis(pentafluoroethyl)phosphinate anion, [(C$_2$F$_5$)$_2$POO]$^-$: 37% uncharacterised compounds: 6%

Example 2

Preparation of ethyl bis(pentafluoroethyl)phosphinate, (C$_2$F$_5$)$_2$P(O)OC$_2$H$_5$, without catalyst (alkali-metal or tetraalkylammonium fluoride)

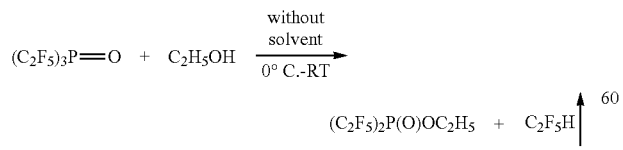

Dry ethanol (0.887 g; 19.3 mmol) is added to cooled (0° C.) tris(pentafluoro-ethyl)phosphine oxide, (C$_2$F$_5$)$_3$P=O, (7.97 g; 19.7 mmol) in a 100 ml glass flask. A two-phase reaction mixture is observed. After 1 h at 0° C., the reaction mixture is a clear and yellow-coloured solution, which is warmed to room temperature and stirred for a total of 47 h. With increasing time at room temperature, the solution becomes an orange-brown colour. Composition in the $^{31}$P-NMR spectrum after 47 h at room temperature: ethyl bis(pentafluoroethyl)phosphinate, (C$_2$F$_5$)$_2$P(O)OC$_2$H$_5$: 29% tris(pentafluoroethyl)phosphine oxide, (C$_2$F$_5$)$_3$P=O: 39% bis(pentafluoroethyl)phosphinate anion, [(C$_2$F$_5$)$_2$POO]$^-$: 26% uncharacterised compounds: 6%

Example 3

Preparation of methyl bis(pentafluoroethyl)phosphinate, (C$_2$F$_5$)$_2$P(O)OCH$_3$

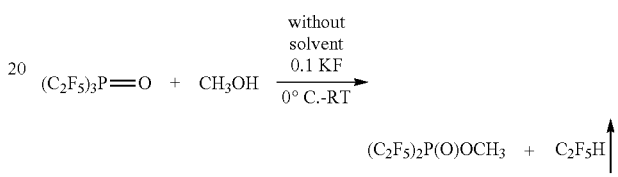

Potassium fluoride (0.85 g; 14.6 mmol) is suspended in tris(pentafluoro-ethyl)phosphine oxide, (C$_2$F$_5$)$_3$P=O, (54.37 g; 134.6 mmol) in a 250 ml glass flask, cooled (0° C.), and dry methanol (4.43 g; 138.2 mmol) is added. The clear and colourless reaction solution is stirred at 0° C. for 1.5 h, warmed and stirred at room temperature for 43 h. After recondensation in vacuo (10$^{-3}$ mbar) at 30° C. and double fractional distillation under reduced pressure (b.p.: 76 to 78° C. at 52 mbar), methyl bis(pentafluoroethyl)phosphinate, (C$_2$F$_5$)$_2$P(O)OCH$_3$, is isolated as clear and colourless liquid (23.65 g; 74.8 mmol) in a yield of 56% and a purity of 98%. The isolated product is characterised by means of $^1$H, $^{19}$F and $^{31}$P NMR spectra in CD$_3$CN.

$^1$H NMR: δ in ppm: 4.24 d (3H), $^3J_{H,P}$=11.1 Hz.
$^{19}$F NMR: δ in ppm: −81.6 m (6F), −124.7 m (4F).
$^{31}$P NMR: δ in ppm: 10.0 quin,m, $^2J_{F,P}$=87.8 Hz.

Example 4

Preparation of 1,3-dimethylimidazolium bis(pentafluoroethyl)phosphinate, [MMIM][(C$_2$F$_5$)$_2$P(O)O]

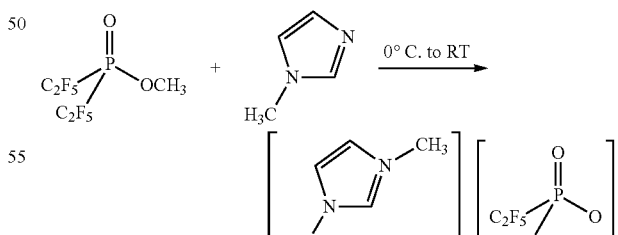

Methyl bis(pentafluoroethyl)phosphinate, (C$_2$F$_5$)$_2$P(O)OCH$_3$, (1.870 g; 5.9 mmol) is slowly added dropwise to cooled (0° C.) N-methylimidazole (0.424 g; 5.2 mmol) (exothermic) in a 25 ml glass flask. A white solid forms. The reaction mixture is diluted with 3.5 ml of n-hexane, warmed to room temperature and stirred for 30 min. The readily volatile constituents are removed in vacuo (10$^{-3}$ mbar) at room temperature. 1,3-Dimethylimidazolium bis(pentafluoroethyl)phosphinate, [MMIM][($C_2F_5$)$_2$P(O)O], (1.982 g; 5.0 mmol) is isolated as white solid in a yield of 96% and a purity of 97%. The isolated product is characterised by means of $^1$H, $^{19}$F and $^{31}$P NMR spectra in $CD_3CN$.

$^1$H NMR: δ in ppm: 8.53 br.s (1H), 7.36 d (2H), $^4J_{H,H}$=1.5; Hz; 3.8 s (6H).

$^{19}$F NMR: δ in ppm: −81.5 m (6F), −126.2 d (4F), $^2J_{F,P}$=65.7 Hz.

$^{31}$P NMR: δ in ppm: −1.5 quin, m, $^2J_{F,P}$=65.8 Hz.

Elemental Analysis

Experimental, %: N, 6.80, C, 27.02 and H, 2.20;

calculated for $C_9H_9F_{10}N_2O_2P$, %: N, 7.04, C, 27.15 and H, 2.28

Example 5

Preparation of methyldiphenylsulfonium bis(pentafluoroethyl)-phosphinate, [$CH_3S(C_6H_5)_2$][($C_2F_5$)$_2$P(O)O]

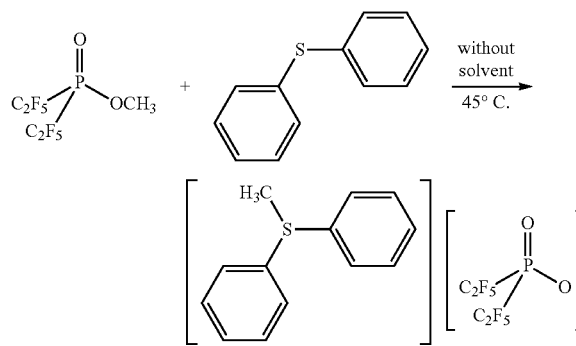

Methyl bis(pentafluoroethyl)phosphinate, ($C_2F_5$)$_2$P(O)OCH$_3$, (1.77 g; 5.6 mmol) is slowly added dropwise to cooled (0° C.) diphenyl sulfide (1.01 g; 5.4 mmol) in a 25 ml glass flask. The two-phase reaction mixture is warmed and stirred at 45° C. for 17 h. The readily volatile constituents are removed in vacuo ($10^{-3}$ mbar) at room temperature. Methyldiphenylsulfonium bis(pentafluoroethyl)phosphinate, [$CH_3S(C_6H_5)_2$][($C_2F_5$)$_2$P(O)O], (2.31 g, 4.6 mmol) is isolated as pale-yellow and highly viscous liquid in a yield of 85% and a purity of 90%.

The isolated product is characterised by means of $^1$H, $^{19}$F and $^{31}$P NMR spectra in $CD_3CN$.

$^1$H NMR: δ in ppm: 7.93 d,m (4H), $^3J_{H,H}$=7.3 Hz; 7.80 t,m (2H), $^3J_{H,H}$=7.5 Hz; 7.71 t,m (4H), $^3J_{H,H}$=7.3 Hz; 3.65 s (3H).

$^{19}$F NMR: δ in ppm: −81.3 m (6F), −126.0 d (4F), $^2J_{F,P}$=70.0 Hz.

$^{31}$P NMR: δ in ppm: −1.2 quin,m, $^2J_{F,P}$=70.0 Hz.

Elemental Analysis

Experimental, %: C, 40.26; H, 2.37; and S, 6.27;

calculated for $C_{17}H_{13}F_{10}O_2PS$, %: C, 40.65; H, 2.61; and S, 6.38;

Example 6

Preparation of N,N-dimethylpyrrolidinium bis(pentafluoroethyl)-phosphinate, [MMPL][($C_2F_5$)$_2$P(O)O]

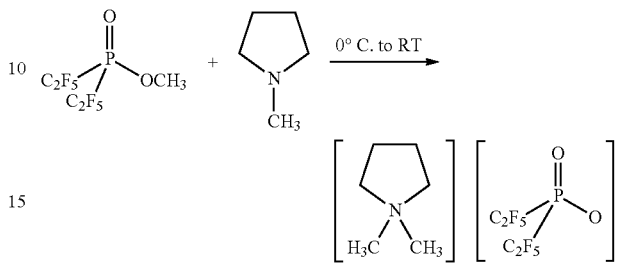

Methyl bis(pentafluoroethyl)phosphinate, ($C_2F_5$)$_2$P(O)OCH$_3$, (3.15 g; 10.0 mmol) is slowly added dropwise to dry, cooled (0° C.) N-methylpyrrolidine (0.85 g; 10.0 mmol) (exothermic) in a 25 ml glass flask. A white suspension forms. The reaction mixture is diluted with 2 ml of n-hexane, warmed to room temperature and stirred for 30 min. The readily volatile constituents are removed in vacuo ($10^{-3}$ mbar) at 35° C. N,N-Dimethylpyrrolidinium bis(pentafluoroethyl)phosphinate, [MMPL][($C_2F_5$)$_2$P(O)O], (2.72 g; 6.8 mmol) is isolated as white solid in a yield of 68% and a purity of 98%.

The isolated product is characterised by means of $^1$H, $^{19}$F and $^{31}$P NMR spectra in $CD_3CN$.

$^1$H NMR: δ in ppm: 3.45 t,m (4H), $^3J_{H,H}$=7.3 Hz, 3.07 s (6H), 2.20 m (4H).

$^{19}$F NMR: δ in ppm −81.5 m (6F), −126.1 d (4F), $^2J_{F,P}$=65.4 Hz. $^{31}$P NMR: δ in ppm −1.7 quin,m, $^2J_{F,P}$=65.4 Hz.

Melting point: 121° C.

Elemental Analysis

Experimental, %: N, 3.53, C, 30.06 and H, 3.49;

calculated for $C_{10}H_{14}F_{10}NO_2P$, %: N, 3.49, C, 29.94 and H, 3.52.

Example 7

Preparation of triethylmethylammonium bis(pentafluoroethyl)-phosphinate, [$CH_3N(C_2H_5)_3$][($C_2F_5$)$_2$P(O)O]

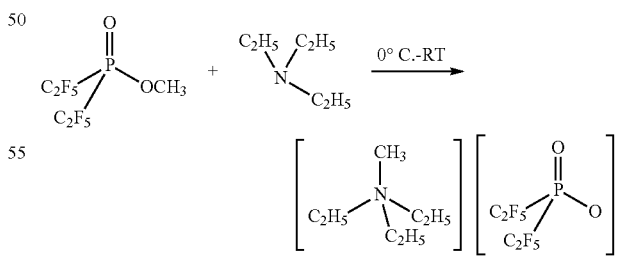

Methyl bis(pentafluoroethyl)phosphinate, ($C_2F_5$)$_2$P(O)OCH$_3$, (1.83 g; 5.8 mmol) is slowly added dropwise to dry and cooled (0° C.) triethylamine (0.59 g; 5.9 mmol) (exothermic) in a 10 ml glass flask. A yellow solid forms. The reaction mixture is diluted with 10 ml of n-hexane, warmed to room temperature and stirred for 20 min. The readily volatile constituents are removed in vacuo ($10^{-3}$ mbar) at room temperature. Triethylmethylammonium bis(pentafluoroethyl)phosphinate, [CH$_3$N(C$_2$H$_5$)$_3$][(C$_2$F$_5$)$_2$P(O)O], (2.19 g; 5.3 mmol) is isolated as pale-yellow solid in a yield of 91% and a purity of 99%.

The isolated product is characterised by means of $^1$H, $^{19}$F and $^{31}$P NMR spectra in CD$_3$CN.

$^1$H NMR: δ in ppm: 3.25 q (6H), $^3$J$_{H,H}$=7.3 Hz, 2.86 s (3H), 1.27 t,m (9H), $^3$J$_{H,H}$=7.3 Hz.

$^{19}$F NMR: δ in ppm: −81.5 m (6F), −126.1 d (4F), $^2$J$_{F,P}$=65.4 Hz.

$^{31}$P NMR: δ in ppm −1.7 quin, m, $^2$J$_{F,P}$=65.5 Hz.

Melting point: 107° C.

Elemental Analysis

Experimental, %: N, 3.40, C, 31.72 and H, 3.54;

calculated for C$_{11}$H$_{18}$F$_{10}$NO$_2$P, %: N, 3.36, C, 31.67 and H, 4.35.

Example 8

Preparation of N,N,N',N',O-pentamethylisouronium bis(pentafluoro-ethyl)phosphinate, [((CH$_3$)$_2$N)$_2$COCH$_3$][(C$_2$F$_5$)$_2$P(O)O]

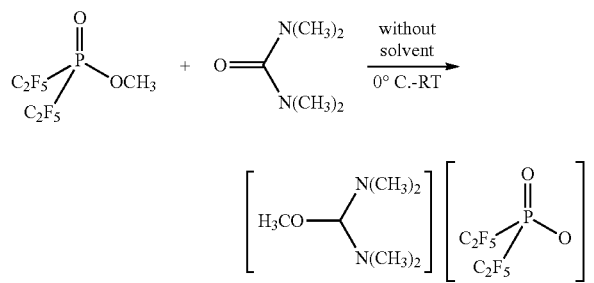

Methyl bis(pentafluoroethyl)phosphinate, (C$_2$F$_5$)$_2$P(O)OCH$_3$, (3.76 g; 11.9 mmol) is slowly added dropwise to dry and cooled (0° C.) N,N,N',N'-tetramethylurea (1.28 g; 11.0 mmol) in a 25 ml glass flask. The colourless reaction solution is warmed (room temperature), stirred for 22.5 h, and the readily volatile constituents are removed in vacuo (10$^{-3}$ mbar) at room temperature. N,N,N',N',O-Pentamethylisouronium bis(pentafluoroethyl)-phosphinate, [((CH$_3$)$_2$N)$_2$COCH$_3$][(C$_2$F$_5$)$_2$P(O)O], (4.73 g; 10.9 mmol) is isolated as colourless, highly viscous liquid in quantitative yield and a purity of 99%.

The isolated product is characterised by means of $^1$H, $^{19}$F and $^{31}$P NMR spectra in CD$_3$CN.

$^1$H NMR: δ in ppm: 4.05 s (3H), 3.05 s (12H)

$^{19}$F NMR: δ in ppm: −81.5 m (6F), −126.1 d (4F), $^2$J$_{F,P}$=65.6 Hz.

$^{31}$P NMR: δ in ppm: −1.6 quin,m, $^2$J$_{F,P}$=65.5 Hz.

Elemental Analysis

Experimental, %: N, 6.36, C, 27.05 and H, 3.23;

calculated for C$_{10}$H$_{16}$F$_{10}$N$_2$O$_3$P, %: N, 6.47, C, 27.73 and H, 3.72.

Example 9

Preparation of N,N,N',N',N"-pentamethylguanidinium bis(pentafluoro-ethyl)phosphinate, [((CH$_3$)$_2$N)$_2$CNHCH$_3$][(C$_2$F$_5$)$_2$P(O)O]

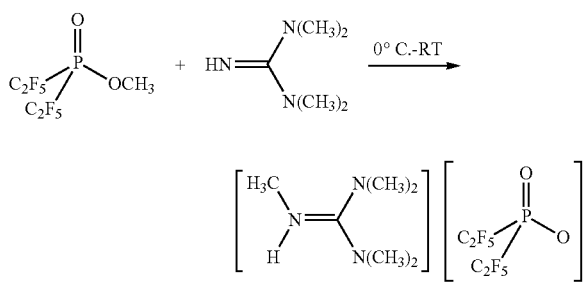

Methyl bis(pentafluoroethyl)phosphinate, (C$_2$F$_5$)$_2$P(O)OCH$_3$, (3.22 g; 10.2 mmol) is slowly added dropwise to dry and cooled (0° C.) 1,1,2,2-tetra-methylguanidine (1.12 g; 9.7 mmol) (exothermic) in a 25 ml glass flask. The cloudy, highly viscous liquid formed spontaneously is warmed (room temperature), diluted with 10 ml of n-hexane, and the reaction mixture is stirred for 3 h. The readily volatile constituents are removed in vacuo (10$^{-3}$ mbar) at 40° C. N,N,N',N',N"-Pentamethylguanidinium bis(pentafluoroethyl)-phosphinate, [((CH$_3$)$_2$N)$_2$CNHCH$_3$][(C$_2$F$_5$)$_2$P(O)O], (4.04 g; 9.4 mmol) is isolated as colourless, cloudy and highly viscous liquid in a yield of 97% and a purity of 88%.

The isolated product is characterised by means of $^1$H, $^{19}$F and $^{31}$P NMR spectra in CD$_3$CN.

$^1$H NMR: δ in ppm: 6.67 s (1H), 2.94 s (3H), 2.92 s (6H), 2.90 s (6H).

$^{19}$F NMR: δ in ppm: −81.5 m (6F), −126.1 d (4F), $^2$J$_{F,P}$=66.1 Hz.

$^{31}$P NMR: δ in ppm: −1.6 quin,m, $^2$J$_{F,P}$=66.1 Hz.

Elemental Analysis

Experimental, %: N, 9.83, C, 28.00 and H, 3.86;

calculated for C$_{10}$H$_{16}$F$_{10}$N$_3$O$_2$P, %: N, 9.74, C, 27.85 and H, 3.74.

Example 10

Preparation of N,N-butylmethylpyrrolidinium bis(pentafluoroethyl)-phosphinate, [BMPL][(C$_2$F$_5$)$_2$P(O)O]

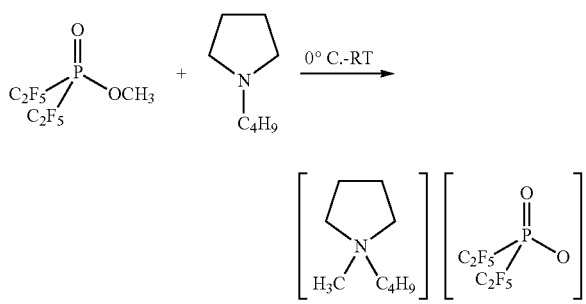

Methyl bis(pentafluoroethyl)phosphinate, $(C_2F_5)_2P(O)OCH_3$, (3.67 g; 11.6 mmol) is slowly added dropwise to dry and cooled (0° C.) N-butyl-pyrrolidine (1.38 g; 11.2 mmol) (exothermic) in a 25 ml glass flask. A pale-yellow solid forms. The reaction mixture is warmed to room temperature, diluted with 10 ml of n-hexane and stirred for 16.5 h. The readily volatile constituents are removed in vacuo ($10^{-3}$ mbar) at room temperature. N-Butyl-N-methylpyrrolidinium bis(pentafluoroethyl)phosphinate, $[BMPL][(C_2F_5)_2P(O)O]$, (4.71 g; 10.7 mmol) is isolated as pale-yellow solid in a yield of 96% and a purity of 99%.

The isolated product is characterised by means of $^1H$, $^{19}F$ and $^{31}P$ NMR spectra in $CD_3CN$.

$^1H$ NMR: δ in ppm: 3.43 m (4H), 3.25 m (2H), 2.96 s (3H), 2.17 m (4H), 1.74 m (2H), 1.40 t,q (2H), $^3J_{H,H}$=7.5 Hz, 0.99 t (3H), $^3J_{H,H}$=7.3 Hz.

$^{19}F$ NMR: δ in ppm: −81.5 m (6F), 126.1 d (4F), $^2J_{F,P}$=65.6 Hz.

$^{31}P$ NMR: δ in ppm: −1.6 quin,m, $^2J_{F,P}$=65.6 Hz.

Melting point: 118° C.

Elemental Analysis

Experimental, %: N, 3.16, C, 35.48 and H, 4.47;

calculated for $C_{13}H_{20}F_{10}NO_2P$, %: N, 3.16, C, 35.23 and H, 4.55.

Example 11

Preparation of 1-ethyl-3-methylimidazolium bis(pentafluoroethyl)-phosphinate, $[EMIM][(C_2F_5)_2P(O)O]$

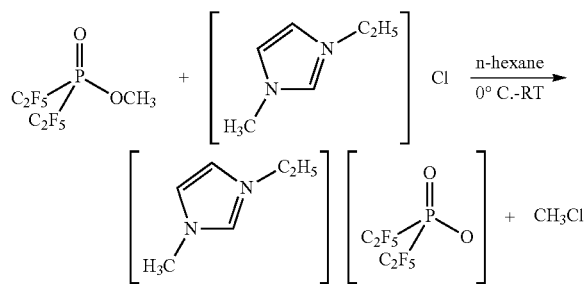

Purified 1-ethyl-3-methylimidazolium chloride, [EMIM] Cl, (0.304 g; 2.1 mmol) is suspended in n-hexane (about 4 ml) in a 10 ml glass flask, cooled (0° C.), and methyl bis(pentafluoroethyl)phosphinate, $(C_2F_5)_2P(O)OCH_3$, (0.676 g; 2.1 mmol) is added. The reaction mixture is warmed (room temperature) and stirred for 26 h. The readily volatile constituents are removed in vacuo ($10^{-3}$ mbar) at room temperature. 1-Ethyl-3-methylimidazolium bis(pentafluoroethyl)phosphinate, $[EMIM][(C_2F_5)_2P(O)O]$, (0.86 g; 2.1 mmol) is isolated as pale-yellow, highly viscous liquid in quantitative yield with a purity of 99%.

The isolated product is characterised by means of $^1H$, $^{19}F$ and $^{31}P$ NMR spectra in $CD_3CN$.

$^1H$ NMR: δ in ppm: 8.77 br.s (1H), 7.47 d,d (1H), $^3J_{H,H}$=1.8 Hz; 7.41 d,d (1H), $^3J_{H,H}$=1.8 Hz; 4.20 q (2H), $^3J_{H,H}$=7.3 Hz; 3.85 s (3H); 1.47 t (3H), $^3J_{H,H}$=7.3 Hz.

$^{19}F$ NMR: δ in ppm: −81.5 m (6F), −126.2 d (4F), $^2J_{F,P}$=66.8 Hz.

$^{31}P$ NMR: δ in ppm: −1.4 quin,m, $^2J_{F,P}$=66.9 Hz.

Example 12

Preparation of ethyl bis(pentafluoroethyl)phosphinate, $(C_2F_5)_2P(O)OC_2H_5$

A) KF as Catalyst

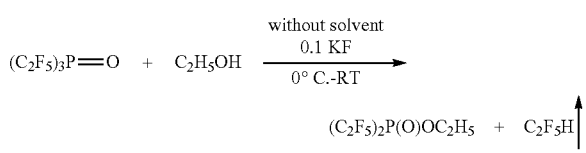

Potassium fluoride (0.515 g; 8.9 mmol) is suspended in tris(pentafluoro-ethyl)phosphine oxide, $(C_2F_5)_3P=O$, (33.02 g; 81.7 mmol) in a 100 ml glass flask, cooled (0° C.), and dry ethanol (3.84 g; 83.3 mmol) is added. The clear and colourless reaction solution is stirred at 0° C. for 1 h and at room temperature for 20.5 h. After recondensation in vacuo ($10^{-3}$ mbar) at 25° C. and subsequent fractional distillation under reduced pressure (b.p.: 69 to 70° C. at 38 mbar), ethyl bis(pentafluoroethyl)phosphinate, $(C_2F_5)_2P(O)OC_2H_5$, is isolated as clear and colourless liquid (16.04 g; 48.6 mmol) in a yield of 59% and a purity of 98%.

The isolated product is characterised by means of $^1H$, $^{19}F$ and $^{31}P$ NMR spectra in $CD_3CN$.

$^1H$ NMR: δ in ppm: 4.68 d,q (2H), $^3J_{H,P}$=8.3 Hz, $^3J_{H,H}$=7.1 Hz, 1.49 t (3H), $^3J_{H,H}$=7.1 Hz.

$^{19}F$ NMR: δ in ppm: −81.5 m (6F), −124.8 m (4F).

$^{31}P$ NMR: δ in ppm: 8.4 quin, $^2J_{F,P}$=87.8 Hz.

Elemental Analysis

Experimental, %: C, 21.27 and H, 1.32;

calculated for $C_6H_5F_{10}O_2P$, %: C, 21.83 and H, 1.53.

B) NaF as Catalyst

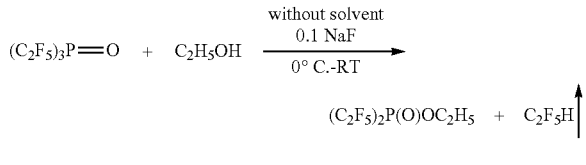

Sodium fluoride (0.043 g; 1.0 mmol) is suspended in tris(pentafluoroethyl)-phosphine oxide, $(C_2F_5)_3P=O$, (3.701 g; 9.2 mmol) in a 25 ml glass flask, cooled (0° C.), and dry ethanol (0.446 g; 9.7 mmol) is added. The clear and colourless reaction solution is stirred at 0° C. for 1 h, warmed and stirred at room temperature for 3.5 h. The formation of $(C_2F_5)_2P(O)OC_2H_5$ with a yield of 88% (detected by means of $^{31}P$ and $^{19}F$ NMR) is observed. Ethyl bis-(pentafluoroethyl)phosphinate, $(C_2F_5)_2P(O)OC_2H_5$, is isolated as clear and colourless liquid using the method described in Example 12 A.

C) RbF as Catalyst

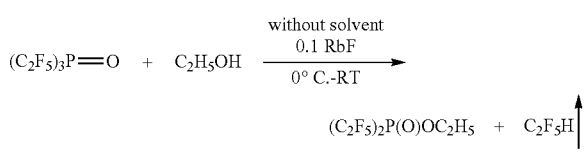

Rubidium fluoride (0.101 g; 1.0 mmol) is suspended in tris(pentafluoro-ethyl)phosphine oxide, $(C_2F_5)_3P=O$, (3.261 g; 8.1 mmol) in a 100 ml glass flask, cooled (0° C.), and dry ethanol (0.406 g; 8.8 mmol) is added. The clear and colourless reaction solution is stirred at 0° C. for 1 h, warmed and stirred at room temperature for 3.5 h. The formation of $(C_2F_5)_2P(O)OC_2H_5$ with a yield of 83% (detected by means of $^{31}P$ and $^{19}F$ NMR) is observed. Ethyl bis(pentafluoroethyl) phosphinate, $(C_2F_5)_2P(O)OC_2H_5$, are isolated as clear and colourless liquid using the method described in Example 12 A.

D) CsF as Catalyst

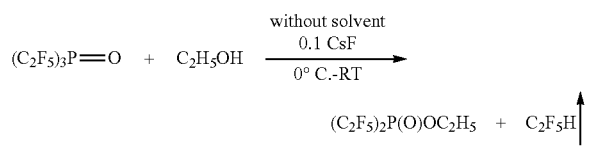

Caesium fluoride (0.149 g; 1.0 mmol) is suspended in tris(pentafluoroethyl)-phosphine oxide, $(C_2F_5)_3P=O$, (3.732 g; 9.2 mmol) in a 100 ml glass flask, cooled (0° C.), and dry ethanol (0.481 g; 10.4 mmol) is added. The clear and colourless reaction solution is stirred at 0° C. for 1 h, warmed and stirred at room temperature for 3.5 h. The formation of $(C_2F_5)_2P(O)OC_2H_5$ with a yield of 84% (detected by means of $^{31}P$ and $^{19}F$ NMR) is observed. Ethyl bis-(pentafluoroethyl)phosphinate, $(C_2F_5)_2P(O)OC_2H_5$, can be isolated as clear and colourless liquid using the method described in Example 12 A.

E) [N(CH$_3$)$_4$]F as Catalyst

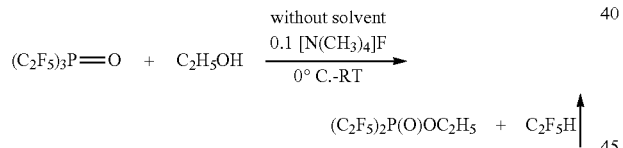

Tetramethylammonium fluoride (0.095 g; 1.0 mmol) is suspended in tris-(pentafluoroethyl)phosphine oxide, $(C_2F_5)_3 P=O$, (3.835 g; 9.5 mmol) in a 25 ml glass flask, cooled (0° C.), and dry ethanol (0.502 g; 10.9 mmol) is added. The clear and colourless reaction suspension is stirred at 0° C. for 1 h, warmed and stirred at room temperature for 3.5 h. The formation of $(C_2F_5)_2P(O)OC_2H_5$ with a yield of 93% (detected by means of $^{31}P$ and $^{19}F$ NMR) is observed. Ethyl bis(pentafluoroethyl)phosphinate, $(C_2F_5)_2P(O)OC_2H_5$, can be isolated as clear and colourless liquid using the method described in Example 12 A.

The isolated product is characterised by means of $^1H$, $^{19}F$ and $^{31}P$ NMR spectra in CD$_3$CN.

$^1H$ NMR: δ in ppm: 0.79 t (3H), $^3J_{H,H}$=7.2 Hz, 3.91 d,q (2H), $^3J_{H,H}$=7.2 Hz, $^3J_{H,P}$=8.2 Hz.

$^{19}F$ NMR: δ in ppm: −82.9 m (6F), −126.1 m (4F).

$^{31}P$ NMR: δ in ppm: 8.5 quin,m, $^2J_{F,P}$=89.2 Hz.

Example 13

Preparation of pentadeuteroethyl bis(pentafluoroethyl)phosphinate, $(C_2F_5)_2P(O)OC_2D_5$

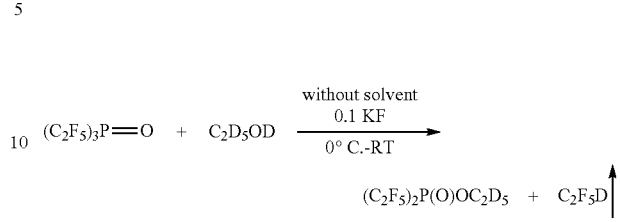

Potassium fluoride (0.105 g; 1.8 mmol) is suspended in cooled (0° C.) tris-(pentafluoroethyl)phosphine oxide, $(C_2F_5)_3 P=O$, (6.727 g; 16.7 mmol) in a 100 ml glass flask, and hexadeuteroethanol (0.928 g; 17.8 mmol) is added. The clear and colourless reaction solution is stirred at 0° C. for 1 h, warmed and stirred at room temperature for 5 h. After recondensation in vacuo ($10^{-3}$ mbar) at room temperature, pentadeuteroethyl bis(pentafluoroethyl)-phosphinate, $(C_2F_5)_2 P(O)OC_2D_5$, is isolated as clear and colourless liquid (4.40 g; 13.1 mmol) in a yield of 78% and a purity of 96%.

The isolated product is characterised by means of $^{19}F$ and $^{31}P$ NMR spectra in CD$_3$CN.

$^{19}F$ NMR: δ in ppm: −82.9 m (6F), −126.2 m (4F).

$^{31}P$ NMR: δ in ppm: 8.3 quin, m, $^2J_{F,P}$=88.1 Hz.

Example 14

Preparation of ethylmethylphenylsulfonium bis(pentafluoroethyl)phosphinate, [(CH$_3$)(C$_2$H$_5$)(C$_6$H$_5$)S][(C$_2$F$_5$)$_2$P(O)O]

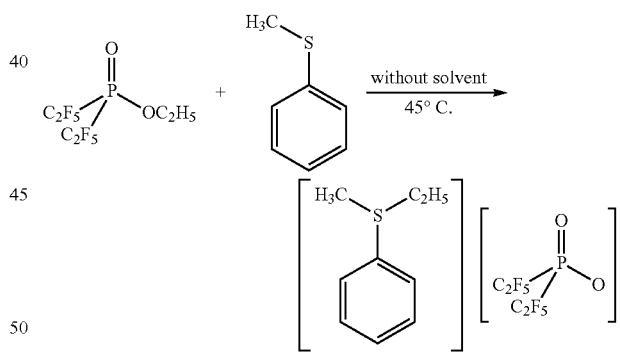

Ethyl bis(pentafluoroethyl)phosphinate, $(C_2F_5)_2P(O)OC_2H_5$, (4.247 g; 12.9 mmol) is added to thioanisole (1.553 g; 12.5 mmol) in a 25 ml glass flask. The reaction emulsion is warmed and stirred at 45° C. for 9 h. The more highly viscous, clear and colourless liquid forms. The readily volatile constituents are removed in vacuo ($10^{-3}$ mbar) at room temperature. Ethylmethylphenylsulfonium bis(pentafluoroethyl) phosphinate, [(CH$_3$)(C$_2$H$_5$)(C$_6$H$_5$)S][(C$_2$F$_5$)$_2$P(O)O], (5.63 g; 12.4 mmol) is isolated as colourless, highly viscous liquid in quantitative yield and a purity of 98%.

$^1H$ NMR in CD$_3$CN: δ in ppm: 7.99 d, m (2H), $^3J_{H,H}$=7.6 Hz, 7.83 t, m (1H), $^3J_{H,H}$=7.4 Hz, 7.73 t, m (2H), $^3J_{H,H}$=7.9 Hz, 3.66 m (2H), 3.24 s (3H), 1.28 t (3H), $^3J_{H,H}$=7.4 Hz.

$^{19}F$ NMR in CD$_3$CN: δ in ppm: −81.3 s (6F), −126.1 d (6F), $^2J_{F,P}$=66.4 Hz.

$^{31}$P NMR in CD$_3$CN: δ in ppm: −1.4 quin,m, $^2J_{F,P}$=66.8 Hz.

Elemental Analysis

Experimental, %: C, 34.08; H, 2.84; and S, 6.74; calculated for C$_{13}$H$_{13}$F$_{10}$O$_2$PS, %: C, 34.37; H, 2.88; and S, 7.06.

Example 15

Preparation of 1-ethyl-3-methylimidazolium bis(pentafluoroethyl)-phosphinate, [EMIM][(C$_2$F$_5$)$_2$P(O)O]

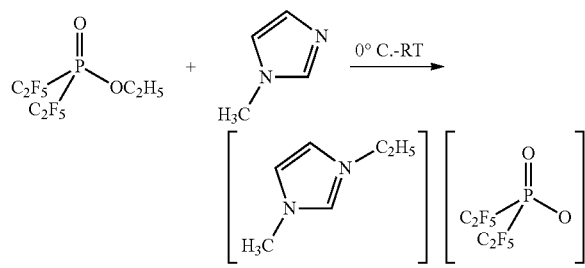

Ethyl bis(pentafluoroethyl)phosphinate, (C$_2$F$_5$)$_2$P(O)OC$_2$H$_5$, (4.59 g; 13.9 mmol) is slowly added dropwise to dry and cooled (0° C.) N-methylimidazole (1.10 g; 13.4 mmol) (exothermic) in a 25 ml glass flask. After 45 minutes, a pale-yellow solid forms. The reaction mixture is warmed to room temperature, diluted with 4 ml of n-hexane and stirred for 45 minutes. The readily volatile constituents are removed in vacuo (10$^{-3}$ mbar) at 40° C. 1-Ethyl-3-methylimidazolium bis(pentafluoroethyl)phosphinate, [EMIM][(C$_2$F$_5$)$_2$P(O)O], (5.52 g; 13.4 mmol) is isolated as highly viscous, pale-yellow liquid in quantitative yield and a purity of 99%.

$^1$H NMR in CD$_3$CN: δ in ppm: 8.92 s (1H), 7.53 d,d (1H), $^3J_{H,H}$=1.8 Hz; 7.45 d,d (1H), $^3J_{H,H}$=1.8 Hz; 4.21 q (2H), $^3J_{H,H}$=7.3 Hz, 3.86 s (3H), 1.47 t (3H), $^3J_{H,H}$=7.3.

$^{19}$F NMR in CD$_3$CN: δ in ppm: −81.5 m (6F), −126.2 d (4F), $^2J_{F,P}$=66.4 Hz.

$^{31}$P NMR in CD$_3$CN: δ in ppm: −1.2 quin,m, $^2J_{F,P}$=66.7 Hz.

Elemental Analysis

Experimental, %: N, 6.78, C, 28.86 and H, 2.78; calculated for C$_{10}$H$_{11}$F$_{10}$N$_2$O$_2$P, %: N, 6.80, C, 29.14 and H, 2.69.

Viscosity Measurement

Dynamic viscosity: η=128 mPa·s (20° C.)
Kinematic viscosity: v=84 mm$^2$/s (20° C.)
Density: ρ=1.527 g/cm$^3$ (20° C.)

Example 16

Preparation of N-ethylpyridinium bis(pentafluoroethyl)phosphinate, [EPy][(C$_2$F$_5$)$_2$P(O)O]

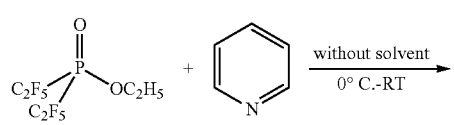

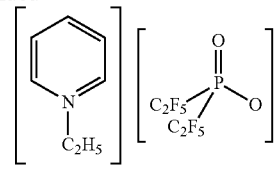

Ethyl bis(pentafluoroethyl)phosphinate, (C$_2$F$_5$)$_2$P(O)OC$_2$H$_5$, (3.956 g; 12.0 mmol) is slowly added dropwise to dry and cooled (0° C.) pyridine (0.941 g; 11.9 mmol) in a 25 ml glass flask. A pale-yellow, more highly viscous solution forms spontaneously. After 30 minutes at 0° C. and 6 h at room temperature, the reaction solution is a brown-orange colour. The readily volatile constituents are removed in vacuo (10$^{-3}$ mbar) at 40° C. N-Ethylpyridinium bis(pentafluoroethyl)phosphinate, [EPy][(C$_2$F$_5$)$_2$P(O)O], (4.845 g; 11.8 mmol) can be isolated as highly viscous, intensely brown-orange liquid in quantitative yield and a purity of 99%.

$^1$H NMR in CD$_3$CN: δ in ppm: 8.88 d (2H), $^3J_{H,H}$=5.7 Hz, 8.54 t,t (1H), $^3J_{H,H}$=7.8 Hz, $^4J_{H,H}$=1.2 Hz, 8.05 m (2H), 4.64 q (2H), $^3J_{H,H}$=7.4, 1.61 t (3H), $^3J_{H,H}$=7.3 Hz.

$^{19}$F NMR in CD$_3$CN: δ in ppm: −81.4 m (6F), −126.1 d (4F), $^2J_{F,P}$=66.1 Hz.

$^{31}$P NMR in CD$_3$CN: δ in ppm: −1.3 quin,m, $^2J_{F,P}$=66.1 Hz.

Elemental Analysis

Experimental, %: N, 3.40, C, 32.28 and H, 2.76; calculated for C$_{11}$H$_{10}$F$_{10}$NO$_2$P, %: N, 3.42, C, 32.29 and H, 2.46.

Viscosity Measurement

Dynamic viscosity: η=97 mPa·s (20° C.)
Kinematic viscosity: v=63 mm$^2$/s (20° C.)
Density: ρ=1.537 g/cm$^3$ (20° C.)

Example 17

Preparation of tributylethylphosphonium bis(pentafluoroethyl)-phosphinate, [(C$_4$H$_9$)$_3$PC$_2$H$_5$][(C$_2$F$_5$)$_2$P(O)O]

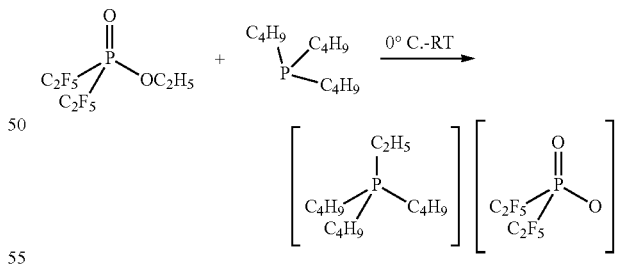

Ethyl bis(pentafluoroethyl)phosphinate (1.538 g; 4.7 mmol) is added to cooled (0° C.) tributylphosphine (0.953 g; 4.7 mmol) in a 25 ml glass flask. The reaction mixture is stirred at 0° C. for 1 h, with initially a two-phase system and later the formation of a solid being observed. The reaction mixture is diluted with 10 ml of n-hexane, warmed and stirred at room temperature for 5.5 h. The readily volatile constituents are removed in vacuo (10$^{-3}$ mbar) at 35° C. Tributylethylphosphonium bis(pentafluoroethyl)phosphinate, [(C$_4$H$_9$)$_3$PC$_2$H$_5$][(C$_2$F$_5$)$_2$P(O)O], (2.262 g; 4.2 mmol) is isolated as colourless solid in a yield of 89% and a purity of 98%.

The isolated product is characterised by means of $^1$H, $^{19}$F and $^{31}$P NMR spectra in CD$_3$CN.

$^1$H NMR: δ in ppm: 2.13 m (8H), 1.50 m (12H), 1.20 d,t (3H), $^3J_{H,P}$=18.2 Hz, $^3J_{H,H}$=7.6 Hz; 0.97 t (9H), $^3J_{H,H}$=7.1 Hz.

$^{19}$F NMR: δ in ppm: −81.4 m (6F), −126.1 d (4F), $^2J_{F,P}$=65.4 Hz.

$^{31}$P NMR: δ in ppm: 35.4 m (1P); −1.7 quin,m, $^2J_{F,P}$=65.3 Hz.

Melting point: 44° C.
Elemental Analysis
Experimental, %: C, 41.20 and H, 6.44;
calculated for C$_{18}$H$_{32}$F$_{10}$NO$_2$P$_2$, %: C, 40.61 and H, 6.06

Example 18

Preparation of 2-(allyloxy)ethyl bis(pentafluoroethyl)phosphinate, (C$_2$F$_5$)$_2$P(O)OCH$_2$CH$_2$OCH$_2$CH=CH$_2$

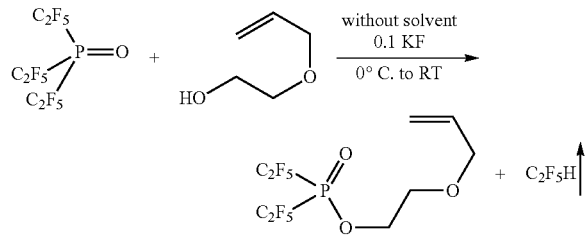

Potassium fluoride (0.277 g; 4.8 mmol) is suspended in tris(pentafluoro-ethyl)phosphine oxide, (C$_2$F$_5$)$_3$P=O, (16.783 g; 41.5 mmol) in a 100 ml glass flask, cooled (0° C.), and 2-allyloxyethanol (4.188 g; 41.0 mmol) is added. The two-phase reaction suspension is stirred at 0° C. for 3 h and at room temperature for 20 h. After recondensation in vacuo (10$^{-3}$ mbar) at 50° C. (decomposition is observed from 40° C.) and subsequent fractional distillation under reduced pressure (b.p.: 40 to 42° C. at 3.8·10$^{-3}$ mbar), 2-(allyloxy)-ethyl bis(pentafluoroethyl)phosphinate, (C$_2$F$_5$)$_2$P(O)OCH$_2$CH$_2$OCH$_2$—CH=CH$_2$, can be isolated as clear and colourless liquid (7.083 g; 18.3 mmol) in a yield of 45% and a purity of 96%. The product is stored at −20° C.

$^1$H NMR in CD$_3$CN: δ in ppm: 5.93 m (1H), 5.32 d,m (1H), $^3J_{trans(H,H)}$=17.1 Hz; 5.20 d,m (1H), $^3J_{cis(H,H)}$=10.5 Hz, 4.69 m (2H); 4.04 d,m (2H), $^3J_{H,H}$=5.5 Hz, 3.75 m (2H).

$^{19}$F NMR in CD$_3$CN: δ in ppm: −81.3 m (6F), −124.4 m (4F).

$^{31}$P NMR in CD$_3$CN: δ in ppm: 8.8 quin,m, $^2J_{F,P}$=88.4 Hz.

Example 19

Preparation of N-[2-(allyloxy)ethyl]pyridinium bis(pentafluoroethyl)-phosphinate, [CH$_2$=CHCH$_2$OCH$_2$CH$_2$Py][(C$_2$F$_5$)$_2$P(O)O]

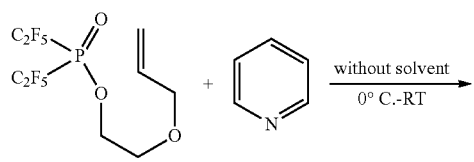

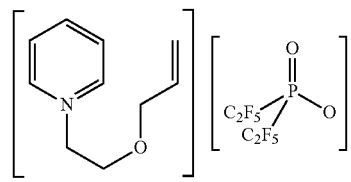

2-(Allyloxy)ethyl bis(pentafluoroethyl)phosphinate, (C$_2$F$_5$)$_2$P(O)O—CH$_2$CH$_2$OCH$_2$CH=CH$_2$, (2.407 g; 6.2 mmol) is slowly added dropwise to dry and cooled (0° C.) pyridine (0.502 g; 6.3 mmol) in a 25 ml glass flask. An orange, more highly viscous solution forms spontaneously, which is stirred at 0° C. for 1 h, warmed and stirred at room temperature for 2 h. The readily volatile constituents are removed in vacuo (10$^{-3}$ mbar) at room temperature. N-[2-(Allyloxy)ethyl]pyridinium bis(pentafluoroethyl)phosphinate, [CH$_2$=CHCH$_2$OCH$_2$CH$_2$Py][(C$_2$F$_5$)$_2$P(O)O], is isolated (2.829 g; 6.1 mmol) as highly viscous, intensely red-brown liquid in quantitative yield and a purity of 89%.

$^1$H NMR in CD$_3$CN: δ in ppm: 8.87 d,m (2H), $^3J_{H,H}$=5.4 Hz, 8.57 t,t (1H), $^3J_{H,H}$=7.8 Hz, $^4J_{H,H}$=1.3 Hz, 8.07 t (2H), $^3J_{H,H}$=7.1 Hz, 5.80 m (1H), 5.19 d,m (1H), $^3J_{trans(H,H)}$=17.3 Hz, 5.14 d,m (1H), $^3J_{cis(H,H)}$=10.5 Hz, 4.78 m (2H), 3.97 d,m (2H), $^3J_{H,H}$=5.4 Hz; 3.90 t (2H), $^3J_{H,H}$=4.9 Hz.

$^{19}$F NMR in CD$_3$CN: δ in ppm: −81.4 m (6F), −126.1 d (4F), $^2J_{F,P}$=66.2 Hz.

$^{31}$P NMR in CD$_3$CN: δ in ppm: −1.3 quin,m, $^2J_{F,P}$=66.2 Hz.

Elemental Analysis
Experimental, %: N, 3.01, C, 36.14 and H, 3.03;
calculated for C$_{14}$H$_{14}$F$_{10}$NO$_3$P, %: N, 2.80, C, 35.96 and H, 3.10.

Example 20

Preparation of 3-[2-(allyloxy)ethyl]-1-methylimidazolium bis(penta-fluroethyl)phosphinate, [CH$_2$=CHCH$_2$OCH$_2$CH$_2$MIM][(C$_2$F$_5$)$_2$P(O)O]

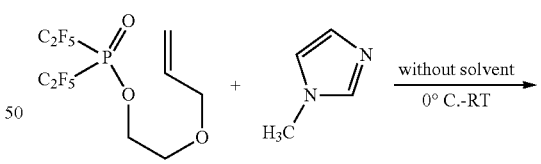

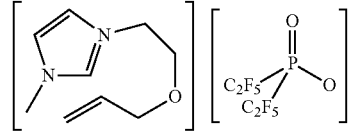

2-(Allyloxy)ethyl bis(pentafluoroethyl)phosphinate, (C$_2$F$_5$)$_2$P(O)OCH$_2$CH$_2$—OCH$_2$CH=CH$_2$, (4.135 g; 10.7 mmol) is slowly added dropwise to dry and cooled (0° C.) N-methylimidazole (0.793 g; 9.7 mmol) (exothermic) in a 50 ml glass flask. A pale-yellow, more highly viscous solution forms spontaneously, which is stirred at 0° C. for 1.5 h, warmed and stirred at room temperature for 5 h. The readily volatile constituents are removed in vacuo ($10^{-3}$ mbar) at room temperature. 3-[2-(Allyloxy)ethyl]-1-methylimidazolium bis(pentafluoroethyl)phosphinate, [CH$_2$=CHCH$_2$OCH$_2$CH$_2$MIM][(C$_2$F$_5$)$_2$—P(O)O], (4.521 g; 9.7 mmol) is isolated as highly viscous, pale-yellow liquid in quantitative yield and a purity of 94%.

$^1$H NMR in CD$_3$CN: δ in ppm: 8.81 s (1H), 7.51 d,d (1H), $^4J_{H,H}$=1.8 Hz, 7.45 d,d (1H), $^4J_{H,H}$=1.8 Hz, 5.88 m (1H), 5.25 d,m (1H), $^3J_{trans(H,H)}$=17.3 Hz; 5.17 d,m (1H), $^3J_{cis(H,H)}$=10.5 Hz, 4.35 m (2H), 4.00 d,m (2H), $^3J_{H,H}$=5.5 Hz, 3.88 s (3H), 3.76 m (2H).

$^{19}$F NMR in CD$_3$CN: δ in ppm: −81.4 m (6F), −126.2 d (4F), $^2J_{F,P}$=66.6 Hz.

$^{31}$P NMR in CD$_3$CN: δ in ppm: −1.3 quin,m, $^2J_{F,P}$=66.8 Hz.

Elemental Analysis

Experimental, %: N, 5.78, C, 33.09 and H, 3.17;

calculated for C$_{13}$H$_{15}$F$_{10}$N$_2$O$_3$P, %: N, 5.98, C, 33.34 and H, 3.23.

Example 21

Preparation of 2-(2',2',2'-trifluoroethoxy)ethyl bis(pentafluoroethyl)-phosphinate, (C$_2$F$_5$)$_2$P(O)OCH$_2$CH$_2$OCH$_2$CF$_3$

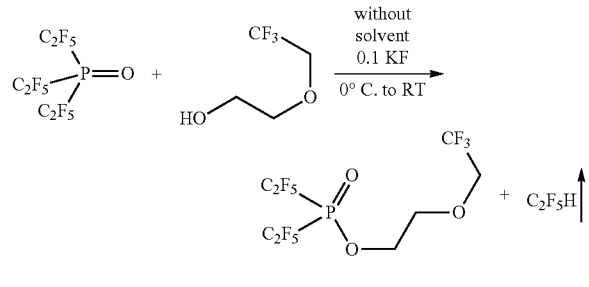

Potassium fluoride (0.228 g; 3.9 mmol) is suspended in tris(pentafluoro-ethyl)phosphine oxide, (C$_2$F$_5$)$_3$P=O, (14.697 g; 36.4 mmol) in a 100 ml glass flask, cooled (0° C.), and 2,2,2-trifluoroethoxyethanol (5.184 g; 36.0 mmol) is added. The white reaction suspension is stirred at 0° C. for 2 h and at room temperature for 21.5 h. After recondensation in vacuo ($10^{-3}$ mbar) at 70° C. and subsequent fractional distillation under reduced pressure (b.p.: 27 to 28° C. at 1·$10^{-3}$ mbar), 2-(2',2',2'-trifluoroethoxy)ethyl bis(pentafluoroethyl)-phosphinate, (C$_2$F$_5$)$_2$P(O)OCH$_2$CH$_2$OCH$_2$CF$_3$, is isolated as clear and colourless liquid (6.041 g; 14.1 mmol) in a yield of 39% and a purity of 96%. Decomposition is observed after a few minutes. The product is stored at −20° C.

$^1$H NMR in CD$_3$CN: δ in ppm: 4.70 m (2H), 4.00 q (2H), $^3J_{H,F}$=8.9 Hz, 3.95 m (2H).

$^{19}$F NMR in CD$_3$CN: δ in ppm: −75.3 t (3F), $^3J_{H,F}$=8.9 Hz; −81.3 m (6F); −124.5 m (4F).

$^{31}$P NMR in CD$_3$CN: δ in ppm: 9.0 quin,m, $^2J_{F,P}$=88.6 Hz.

Example 22

Preparation of 1-methyl-3-[2-(2',2',2'-trifluoroethoxy)ethylimidazolium bis(pentafluoroethyl)phosphinate, [CF$_3$CH$_2$OCH$_2$CH$_2$MIM][(C$_2$F$_5$)$_2$—P(O)O]

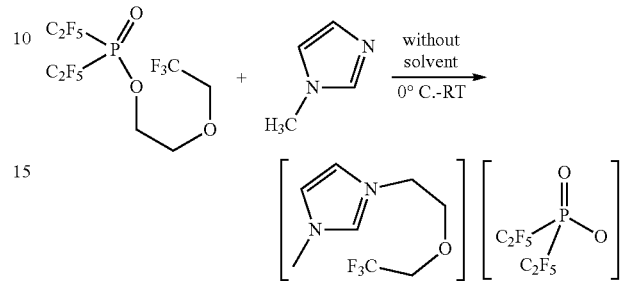

2-(2',2',2'-Trifluoroethoxy)ethyl bis(pentafluoroethyl)phosphinate, (C$_2$F$_5$)$_2$—P(O)OCH$_2$CH$_2$OCH$_2$CF$_3$, (3.589 g; 8.4 mmol) is slowly added dropwise to dry and cooled (0° C.) N-methylimidazole (0.726 g; 8.8 mmol) in a 10 ml glass flask. A pale-yellow, more highly viscous solution forms spontaneously, which is stirred at 0° C. for 1 h, warmed and stirred at room temperature for 3 h. The readily volatile constituents are removed in vacuo ($10^{-3}$ mbar) at room temperature. 1-Methyl-3-[2-(2',2',2'-trifluoroethoxy)-ethylimidazolium bis(pentafluoroethyl)phosphinate, [CF$_3$CH$_2$OCH$_2$CH$_2$MIM][(C$_2$F$_5$)$_2$P(O)O], (4.253 g; 8.3 mmol) is isolated as highly viscous, pale-yellow liquid in quantitative yield and a purity of 95%.

$^1$H NMR in CD$_3$CN: δ in ppm: 8.84 s (1H), 7.51 d,d (1H), $^4J_{H,H}$=1.8 Hz, 7.46 d,d (1H), $^4J_{H,H}$=1.8 Hz, 4.39 m (2H), 4.00 q (2H), $^3J_{H,F}$=9.0 Hz, 3.98 t (2H), $^3J_{H,H}$=4.8 Hz, 3.88 s (3H).

$^{19}$F NMR in CD$_3$CN: δ in ppm: −75.3 t (3H), $^3J_{H,F}$=9.0 Hz, −81.5 m (6F), −126.2 d (4F), $^2J_{F,P}$=66.4 Hz.

$^{31}$P NMR in CD$_3$CN: δ in ppm: −1.3 quin,m, $^2J_{F,P}$=66.4 Hz.

Elemental Analysis

Experimental, %: N, 5.53, C, 28.77 and H, 2.40;

calculated for C$_{12}$H$_{12}$F$_{13}$N$_2$O$_3$P, %: N, 5.49, C, 28.25 and H, 2.37.

Example 23

Preparation of phenyl bis(pentafluoroethyl)phosphinate, (C$_2$F$_5$)$_2$—P(O)OC$_6$H$_5$

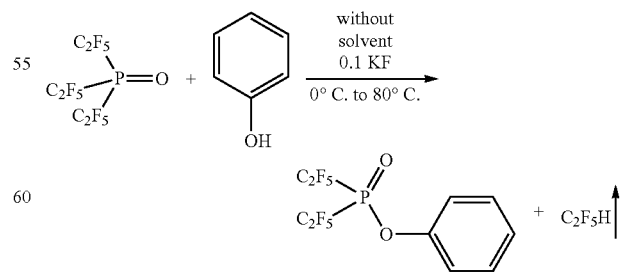

Potassium fluoride (0.122 g; 2.1 mmol) is suspended in cooled (0° C.) tris(pentafluoroethyl)phosphine oxide (7.378 g; 18.3 mmol) in a 100 ml glass flask, and phenol (1.797 g;

19.1 mmol) is added. The reaction suspension is warmed and stirred at 80° C. for 4.5 h. A pale-brown reaction suspension is then observed. After recondensation in vacuo ($10^{-3}$ mbar) at 40° C., phenyl bis(pentafluoroethyl)phosphinate, $(C_2F_5)_2P(O)OC_6H_5$, is isolated as clear and colourless liquid (3.127 g; 8.3 mmol) in a yield of 45% and a purity of 90%.

The isolated product is characterised by means of $^1H$, $^{19}F$ and $^{31}P$ NMR spectra in $CD_3CN$ film.

$^1H$ NMR: δ in ppm: 6.29 m (5H).

$^{19}F$ NMR: δ in ppm: −82.4 m (6F), −124.8 m (4F).

$^{31}P$ NMR: δ in ppm: 4.5 quin,m, $^2J_{F,P}$=91.1 Hz.

Example 24

Preparation of 9-decyl bis(pentafluoroethyl)phosphinate, $(C_2F_5)_2$—$P(O)OCH_2(CH_2)_7CH$=$CH_2$

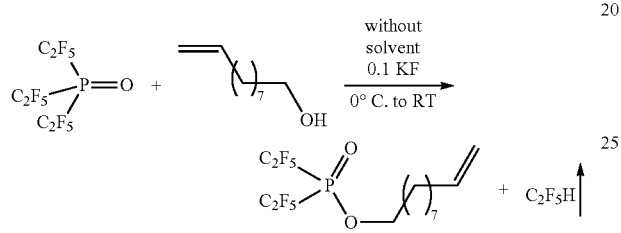

Potassium fluoride (0.138 g; 2.4 mmol) is suspended in tris(pentafluoro-ethyl)phosphine oxide (9.26 g; 22.9 mmol) in a 100 ml glass flask, and 9-decen-1-ol (3.387 g; 21.7 mmol) is added. During the addition, the reaction mixture warms and is cooled (0° C.). When the addition is complete, the orange reaction solution is warmed and stirred at room temperature for 20 h. 9-decyl bis(pentafluoroethyl)phosphinate, $(C_2F_5)_2P(O)\_OCH_2(CH_2)_7CH$=$CH_2$, is isolated as clear and colourless liquid (4.66 g; 10.6 mmol) in a yield of 49% and a purity of 94% by fractional distillation under reduced pressure (b.p.: 70 to 74° C. at $2.5 \cdot 10^{-1}$ mbar).

The isolated product is characterised by means of $^1H$, $^{19}F$ and $^{31}P$ NMR spectra in $CD_3CN$.

$^1H$ NMR: δ in ppm: 5.85 m (1H), 5.02 d,m (1H), $^3J_{trans(H,H)}$=17.1 Hz, 4.98 d, m (1H), $^3J_{cis(H,H)}$=10.2 Hz, 4.61 d, t (2H), $^3J_{(H,P)}$=7.3 Hz, $^3J_{(H,H)}$=6.4 Hz, 2.07 m (2H), 1.82 m (2H), 1.34 m (10H).

$^{19}F$ NMR: δ in ppm: −79.5 m (6F), −122.7 m (4F).

$^{31}P$ NMR: δ in ppm: 7.5 quin, m, $^2J_{F,P}$=88.0 Hz.

Example 25

Preparation of propargyl bis(pentafluoroethyl)phosphinate, $(C_2F_5)_2P(O)OCH_2C$≡$CH$

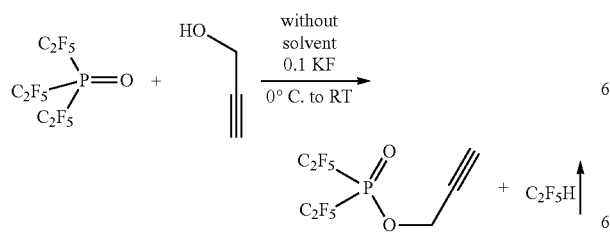

Potassium fluoride (0.262 g; 4.5 mmol) is suspended in cooled (0° C.) tris(pentafluoroethyl)phosphine oxide (14.930 g; 37.0 mmol) in a 100 ml glass flask, and propargyl alcohol (2.055 g; 36.7 mmol) is added. The yellow reaction solution is slowly warmed (about 6 h) and stirred at room temperature for 19.5 h. Volatile components are removed in vacuo ($10^{-3}$ mbar) at 0° C. After recondensation in vacuo ($10^{-3}$ mbar) at room temperature, propargyl bis(pentafluoroethyl)phosphinate, $(C_2F_5)_2P(O)OCH_2C$≡$CH$, is isolated as clear and colourless liquid (7.831 g; 23.0 mmol) in a yield of 63% and a purity of 95%. The ester becomes a brown colour after a few minutes at room temperature and is therefore stored at 3° C.

The isolated product is characterised by means of $^1H$, $^{19}F$ and $^{31}P$ NMR spectra in $CD_3CN$ film.

$^1H$ NMR: δ in ppm: 4.48 d, d (2H), $^3J_{(H,P)}$=10.3 Hz, $^4J_{(H,H)}$=2.2 Hz, 2.29 m (1H).

$^{19}F$ NMR: δ in ppm: −82.5 m (6F), −125.4 m (4F).

$^{31}P$ NMR: δ in ppm: 10.1 quin, m, $^2J_{F,P}$=90.6 Hz.

Example 26

Preparation of 1-propargyl-3-methylimidazolium bis(pentafluoroethyl)-phosphinate, $[CH$≡$CCH_2MIM][(C_2F_5)_2P(O)O]$

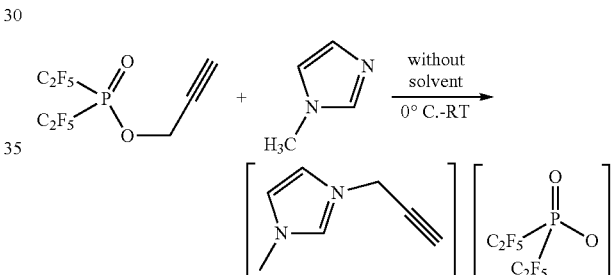

Propargyl bis(pentafluoroethyl)phosphinate (11.18 g; 32.9 mmol) is slowly added dropwise to cooled (0° C.) N-methylimidazole (2.22 g; 27.1 mmol) in a 100 ml glass flask. In an exothermic reaction, an orange solid is formed, which is warmed and stirred at room temperature for 1.5 h. After drying in vacuo ($10^{-3}$ mbar) at room temperature, 1-propargyl-3-methylimidazolium bis(pentafluoroethyl)phosphinate, $[CH$≡$CCH_2MIM][(C_2F_5)_2P(O)O]$, (11.14 g; 26.3 mmol) is isolated as pale-orange solid in a yield of 99% and a purity of 97%. The coloured solid can be washed colourless with dichloromethane and n-hexane.

The isolated product is characterised by means of $^1H$, $^{19}F$ and $^{31}P$ NMR spectra in $CD_3CN$.

$^1H$ NMR: δ in ppm: 8.72 br.s (1H), 7.51 m (1H), 7.42 m (1H), 5.03 d (2H), $^4J_{H,H}$=2.5 Hz, 3.87 s (3H), 3.07 t (1H), $^4J_{H,H}$=2.5 Hz.

$^{19}F$ NMR: δ in ppm: −81.5 m (6F), −126.2 d (4F), $^2J_{F,P}$=65.3 Hz.

$^{31}P$ NMR: δ in ppm: −1.5 quin, $^2J_{F,P}$=65.5 Hz.

Elemental Analysis

Experimental, %: N, 6.55, C, 31.21 and H, 2.02;

Example 27

Preparation of 1-methyl-1-propargylpyrrolidinium bis(pentafluoro-ethyl)phosphinate, [CH≡CCH₂MPL][(C₂F₅)₂P(O)O]

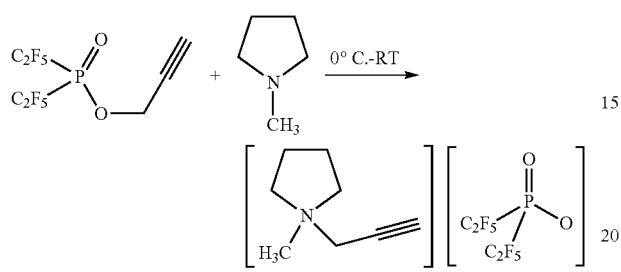

Propargyl bis(pentafluoroethyl)phosphinate (6.44 g; 18.9 mmol) is added to cooled (0° C.) N-methylpyrrolidine (1.60 g; 18.7 mmol) in a 25 ml glass flask. In an exothermic reaction, a yellow solid forms spontaneously. This is suspended in n-hexane (12 ml), stirred at 0° C. for 30 minutes, warmed (room temperature), diluted with further n-hexane (8 ml) and stirred at room temperature for 17 h. The readily volatile constituents are removed in vacuo ($10^{-3}$ mbar) at 50° C. 1-Methyl-1-propargylpyrrolidinium bis(pentafluoro-ethyl)phosphinate, [CH≡CCH₂MPL][(C₂F₅)₂P(O)O], (7.47 g; 17.6 mmol) is isolated as pale-beige solid in a yield of 94% and a purity of 98%.

The isolated product is characterised by means of $^1$H, $^{19}$F and $^{31}$P NMR spectra in CD₃CN.

$^1$H NMR: δ in ppm: 4.21 d (2H), $^4J_{H,H}$=2.5 Hz, 3.56 m (4H), 3.20 t (1H), $^4J_{H,H}$=2.5 Hz, 3.14 s (3H), 2.21 m (4H).

$^{19}$F NMR: δ in ppm: −81.5 m (6F), −126.1 d (4F), $^2J_{F,P}$=65.9 Hz.

$^{31}$P NMR: δ in ppm: −1.5 quin, m, $^2J_{F,P}$=65.9 Hz.

Melting point: 70° C.

Elemental Analysis

Experimental, %: N, 3.30, C, 34.11 and H, 3.34;

calculated for C₁₂H₁₄F₁₀NO₂P, %: N, 3.29, C, 33.90 and H, 3.32

Example 28

Preparation of trioctylpropargylammonium bis(pentafluoroethyl)-phosphinate, [(C₈H₁₇)₃NCH₂C≡CH][(C₂F₅)₂P(O)O]

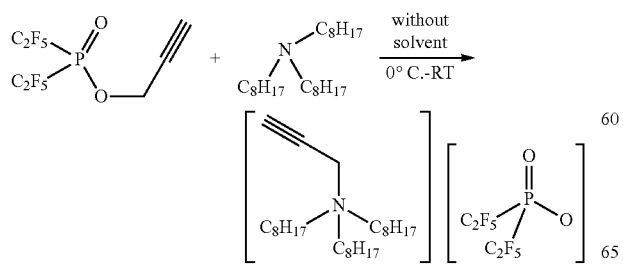

Propargyl bis(pentafluoroethyl)phosphinate (4.131 g; 12.1 mmol) is slowly added dropwise to cooled (0° C.) trioctylamine (4.333 g; 12.3 mmol) in a 100 ml glass flask. An orange, more highly viscous solution forms spontaneously, which is warmed to room temperature. The readily volatile constituents are removed in vacuo ($10^{-3}$ mbar) at room temperature to 120° C. Trioctylpropargylammonium bis(pentafluoroethyl)phosphinate, [(C₈H₁₇)₃—NCH₂C≡CH][(C₂F₅)₂P(O)O], (7.646 g; 11.0 mmol) is isolated as pale-orange liquid in a yield of 91% and a purity of 97%.

The isolated product is characterised by means of $^1$H, $^{19}$F and $^{31}$P NMR spectra in CD₃CN.

$^1$H NMR: δ in ppm: 4.11 m (2H); 3.25 m (6H); 2.92 m (1H); 1.67 m (6H); 1.34 m (30H); 0.92 M (9H).

$^{19}$F NMR: δ in ppm: −81.4 m (6F), −126.1 d (4F), $^2J_{F,P}$=66.0 Hz.

$^{31}$P NMR: δ in ppm: −1.7 quin,m, $^2J_{F,P}$=66.0 Hz.

Elemental Analysis

Experimental, %: N, 2.03, C, 54.79 and H, 8.08;

calculated for C₃₁H₅₄F₁₀NO₂P, %: N, 2.02, C, 53.67 and H, 7.85

Example 29

Preparation of ethyl bis(nonafluorobutyl)phosphinate, (C₄F₉)₂P(O)OC₂H₅

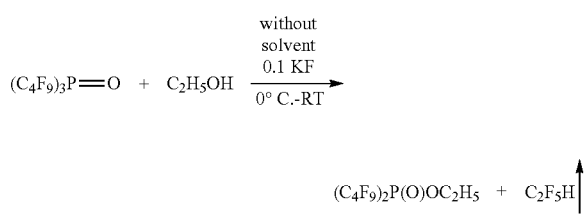

Potassium fluoride (0.158 g; 8.9 mmol) is suspended in cooled (0° C.) tris-(nonafluorobutyl)phosphine oxide, (C₄F₉)₃P=O, (18.57 g; 26.4 mmol) in a 100 ml glass flask, and dry ethanol (1.256 g; 27.3 mmol) is added. The clear and colourless reaction solution is stirred at 0° C. for 2 h and at room temperature for 64.5 h and recondensed in vacuo ($10^{-3}$ mbar) at room temperature to 50° C. After recondensation and subsequent fractional distillation in vacuo ($4.3 \cdot 10^{-3}$ mbar), ethyl bis(nonafluorobutyl)phosphinate, (C₄F₉)₂P(O)OC₂H₅, is isolated as clear and colourless liquid (4.82 g; 9.1 mmol) in a yield of 34% (b.p.: 40-41° C. at $4.3 \cdot 10^{-3}$ mbar).

The isolated product is characterised by means of $^1$H, $^{19}$F and $^{31}$P NMR spectra in CD₃CN.

$^1$H NMR: δ in ppm: 3.78 d,q (2H, CH₂), $^3J_{H,P}$=$^3J_{H,H}$=7.6 Hz, 0.64 t (3H, CH₃), $^3J_{H,H}$=7.1 Hz.

$^{19}$F NMR: δ in ppm: −84.0 t,m (6F, 2CF₃), $^3J_{F,F}$=9.7 Hz, −122.2 m (8F, 4CF₂), −128.4 t,m (4F, 2CF₂), $^3J_{F,F}$=13.7 Hz.

$^{31}$P NMR: δ in ppm: 8.8 quin, $^2J_{F,P}$=90.0 Hz.

Example 30

Preparation of 1-ethyl-3-methylimidazolium bis(nonafluorobutyl)-phosphinate, [EMIM][(C$_4$F$_9$)$_2$P(O)O]

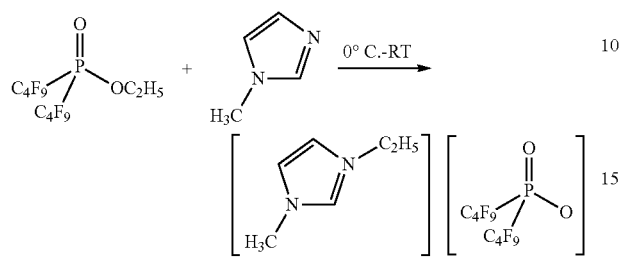

Ethyl bis(nonafluorobutyl)phosphinate, (C$_4$F$_9$)$_2$P(O)OC$_2$H$_5$, (3.834 g; 7.2 mmol) is slowly added to cooled (0° C.) N-methylimidazole (0.458 g; 5.6 mmol) in a 25 ml glass flask. An exothermic reaction and two orange phases are observed. After a few minutes, a green-coloured, more highly viscous solution forms. This is stirred at 0° C. for 2.5 h and at room temperature for 41 h. 1-Ethyl-3-methylimidazolium bis(nonafluorobutyl)phosphinate, [EMIM][(C$_4$F$_9$)$_2$P(O)O], (3.233 g; 5.3 mmol) can be isolated as a highly viscous, green liquid in a yield of 95% and a purity of 95% by purification in vacuo ($10^{-3}$ mbar) at room temperature to 50° C.

The isolated product is characterised by means of $^1$H, $^{19}$F and $^{31}$P NMR spectra in CD$_3$CN.

$^1$H NMR: δ in ppm: 8.82 br.s (1H), 7.48 m (1H); 7.41 m (1H), 4.21 q (2H), $^3J_{H,H}$=7.4 Hz, 3.86 s (3H), 1.47 t (3H), $^3J_{H,H}$=7.4 Hz.

$^{19}$F NMR: δ in ppm: −81.5 t, m (6F), $^3J_{F,F}$=9.9 Hz, −121.7 m (4F), −122.6 d, m (4F), $^2J_{F,P}$=67.7 Hz, 126.5 m (4F).

$^{31}$P NMR: δ in ppm: 0.1 quin, m $^2J_{F,P}$=67.7 Hz.

Elemental Analysis

Experimental, %: N, 4.05; C, 26.79; and H, 1.88;
calculated for C$_{14}$H$_{11}$F$_{18}$N$_2$O$_2$P, %: N, 4.58; C, 27.47; and H, 1.81

Example 31

Preparation of 3-bromopropyl bis(pentafluoroethyl)phosphinate, (C$_2$F$_5$)$_2$P(O)OCH$_2$CH$_2$CH$_2$Br

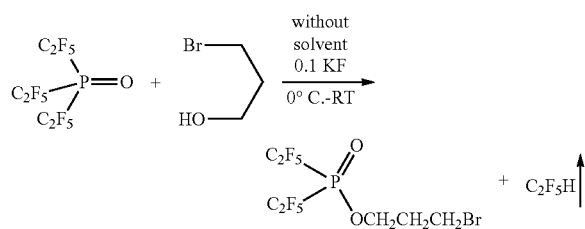

Potassium fluoride (0.227 g; 3.9 mmol) is suspended in cooled (0° C.) tris-(pentafluoroethyl)phosphine oxide, (C$_2$F$_5$)$_3$P=O, (13.773 g; 34.1 mmol) in a 100 ml glass flask, and pale-yellow 3-bromopropan-1-ol (4.790 g; 34.5 mmol) is added. The two-phase reaction mixture is warmed and stirred at room temperature for 20 h. After condensation in vacuo ($10^{-3}$ mbar) at room temperature and double fractional distillation under reduced pressure (b.p.: 76 to 78° C. at 7.6 mbar), 3-bromopropyl bis(pentafluoroethyl)phosphinate, (C$_2$F$_5$)$_2$P(O)OCH$_2$CH$_2$CH$_2$Br, can be isolated as clear and colourless liquid (5.137 g; 12.1 mmol) in a yield of 35% and a purity of 96%.

The isolated product is characterised by means of $^1$H, $^{19}$F and $^{31}$P NMR spectra in CD$_3$CN.

$^1$H NMR: δ in ppm: 4.74 d, t (2H), $^3J_{H,P}$=6.8 Hz, $^3J_{H,H}$=6.0 Hz; 3.56 t (2H), $^3J_{H,H}$=6.4 Hz; 2.36 quin, m (2H), $^3J_{H,H}$=6.2 Hz.

$^{19}$F NMR: δ in ppm: −81.2 m (6F); −124.3 m (4F).

$^{31}$P NMR: δ in ppm: 8.9 quin, m, $^2J_{F,P}$=88.5 Hz.

Example 32

Preparation of 2,2,3,3,4,4,5,5-octafluoropentyl bis(pentafluoroethyl-) phosphinate, (C$_2$F$_5$)$_2$P(O)OCH$_2$CF$_2$CF$_2$CF$_2$CF$_2$H

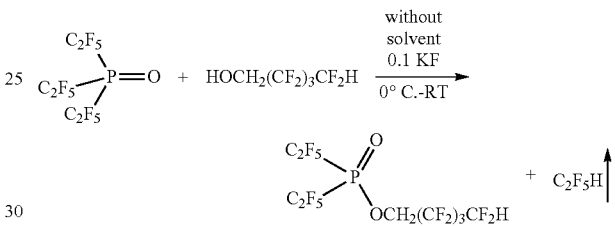

Potassium fluoride (0.185 g; 3.2 mmol) is suspended in cooled (0° C.) tris-(pentafluoroethyl)phosphine oxide, (C$_2$F$_5$)$_3$P=O, (9.957 g; 24.6 mmol) in a 100 ml glass flask, and 2,2,3,3,4,4,5,5-octafluoropentan-1-ol (5.491 g; 23.7 mmol) is added dropwise. The reaction suspension is warmed and stirred at room temperature for 46.5 h. After condensation in vacuo ($10^{-3}$ mbar) at room temperature to 60° C. and double fractional distillation in vacuo ($6.10^{-3}$ mbar) (b.p.: 31 to 32° C.), 2,2,3,3,4,4,5,5-octafluoropentyl bis-(pentafluoroethyl)phosphinate, (C$_2$F$_5$)$_2$P(O)OCH$_2$CF$_2$CF$_2$CF$_2$CF$_2$H, can be isolated as clear and colourless liquid (1.603 g; 3.1 mmol) in a yield of 13% and a purity of 98%.

The isolated product is characterised by means of $^1$H, $^{19}$F and $^{31}$P NMR spectra in CD$_3$CN.

$^1$H NMR: δ in ppm: 6.44 t, t (1H), $^2J_{H,F}$=51.1 Hz, $^3J_{H,F}$=5.3 Hz; 5.11 t, d (2H), $^3J_{H,F}$=12.9 Hz, $^3J_{H,P}$=8.0 Hz.

$^{19}$F NMR: δ in ppm: −81.3 m (6F); −121.7 m (2F); −123.8 m (4F); −125.5 m (2F); −130.7 m (2F); −139.4 d,m (2F), $^2J_{H,F}$=51.1 Hz.

$^{31}$P NMR: δ in ppm: 10.6 quin, m, $^2J_{F,P}$=92.2 Hz.

Example 33

Preparation of 1-(3-bromopropyl)-3-methylimidazolium bis(pentafluoroethyl)phosphinate, [BrCH$_2$CH$_2$CH$_2$MIM][(C$_2$F$_5$)$_2$P(O)O]

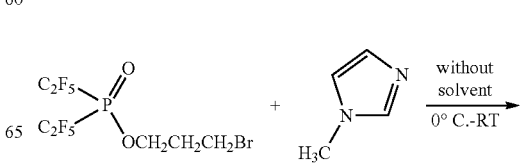

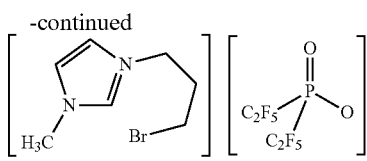

3-Bromopropyl bis(pentafluoroethyl)phosphinate, $(C_2F_5)_2$ $P(O)OCH_2$—$CH_2CH_2Br$, (4.710 g; 11.1 mmol) is slowly added dropwise to cooled (0° C.) N-methylimidazole (0.907 g; 11.0 mmol) (exothermic) in a 50 ml glass flask. It The colourless, more highly viscous and slightly cloudy reaction mixture is stirred at 0° C. for 1 h and at room temperature for 3 h and purified in vacuo ($10^{-3}$ mbar) at room temperature. 1-(3-Bromopropyl)-3-methylimidazolium bis(pentafluoroethyl)phosphinate, $[BrCH_2CH_2CH_2MIM][(C_2F_5)_2P(O)O]$, (5.286 g; 10.5 mmol) can be isolated as colourless, highly viscous and slightly cloudy liquid in a yield of 95% and a purity of 90%.

The isolated product is characterised by means of $^1H$, $^{19}F$ and $^{31}P$ NMR spectra in $CD_3CN$.

$^1$H NMR: δ in ppm: 8.83 br.s (1H); 7.50 d, m (1H), $^4J_{H,H}$=1.8 Hz; 7.44 d, m (1H), $^4J_{H,H}$=1.8 Hz; 4.32 t (2H), $^3J_{H,H}$=7.0 Hz; 3.86 s (3H); 3.46 t (2H), $^3J_{H,H}$=6.5 Hz; 2.40 quin (2H), $^3J_{H,H}$=6.8 Hz.

$^{19}$F NMR: δ in ppm: −81.4 m (6F); −126.1 d (4F), $^2J_{F,P}$=66.3 Hz.

$^{31}$P NMR: δ in ppm: −1.3 quin, m, $^2J_{F,P}$=66.3 Hz.

Elemental Analysis
Experimental, %: N, 6.03, C, 25.84 and H, 2.35;
calculated for $C_{11}H_{12}BrF_{10}N_2O_2P$, %: N, 5.55, C, 23.16 and H, 2.39

Example 34

Preparation of methyltriphenoxyphosphonium bis(pentafluoro-ethyl)phosphinate, $[(C_6H_5O)_3PCH_3][(C_2F_5)_2P(O)O]$

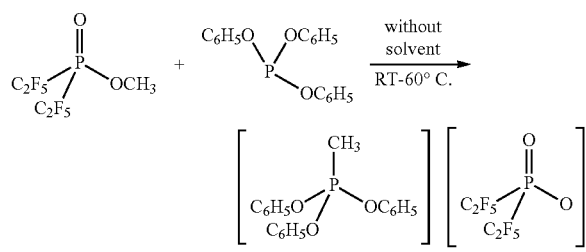

Methyl bis(pentafluoroethyl)phosphinate, $(C_2F_5)_2P(O)OCH_3$, (2.755 g; 8.7 mmol) is added at room temperature to triphenyl phosphite, $P(OC_6H_5)_3$, (2.075 g; 6.7 mmol) in a 10 ml glass flask. The two-phase reaction mixture is warmed and stirred at 60° C. for 5.5 h. A cloudy and colourless reaction mixture forms, that is stirred at RT for 16 h and at 60° C. for 5 h. Methyl bis(pentafluoroethyl)phosphinate, $(C_2F_5)_2P(O)OCH_3$, (0.380 g; 1.2 mmol) is added again, and the mixture is again stirred at 60° C. for 5.5 h. Methyltriphenoxyphosphonium bis(pentafluoroethyl)phosphinate, $[(C_6H_5O)_3PCH_3]$-$[(C_2F_5)_2P(O)O]$, can be isolated as white and crystalline solid (3.827 g; 6.1 mmol) in a yield of 91% and a purity of 89% by purification in vacuo ($10^{-3}$ mbar) at 80° C.

The isolated product is characterised by means of $^1H$, $^{19}F$ and $^{31}P$ NMR spectra in $CD_3CN$.

$^1$H NMR: δ in ppm: 7.56 t, m (6H), $^3J_{H,H}$=7.8 Hz; 7.49 t, m (3H), $^3J_{H,H}$=7.3 Hz; 7.35 d, m (6H), $^3J_{H,H}$=7.8 Hz; 2.62 d (3H), $^2J_{H,P}$=17.0 Hz.

$^{19}$F NMR: δ in ppm: −81.4 m (6F); −126.1 d (4F), $^2J_{F,P}$=72.6 Hz.

$^{31}$P NMR: δ in ppm: 41.5 q (1P), $^2J_{H,P}$=17.0 Hz; −1.1 quin, m (1P), $^2J_{F,P}$=72.6 Hz.

Elemental Analysis
Experimental, %: C, 43.45 and H, 2.91;
calculated for $C_{23}H_{15}F_{10}O_5P_2$, %: C, 44.11 and H, 2.90

Example 35

Preparation of 2-tris(pentafluoroethyl)-1,3,2-dioxaphosphinane, $(C_2F_5)_3P(O_2C_3H_6)$

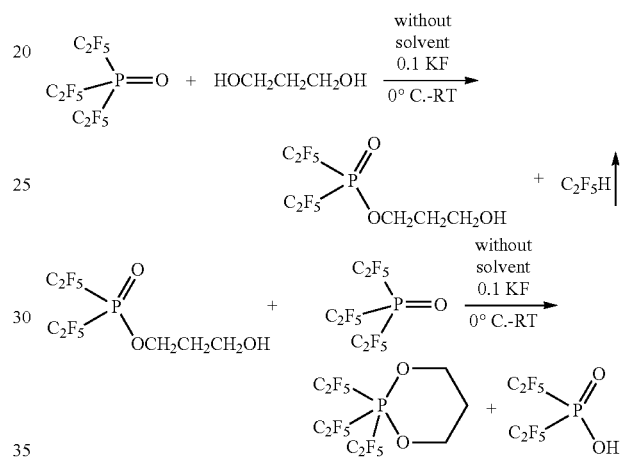

Potassium fluoride (0.069 g; 1.2 mmol) is suspended in cooled (0° C.) tris-(pentafluoroethyl)phosphine oxide, $(C_2F_5)_3$ P=O, (4.131 g; 10.2 mmol) in a 25 ml flask, and propane-1,3-diol (0.800 g; 10.5 mmol) is added. The colourless reaction suspension is stirred at 0° C. for 1.5 h and at RT for 48 h and subsequently condensed at RT in vacuo. 2-Tris(pentafluoroethyl)-1,3,2-dioxaphosphinane is isolated as colourless solid (0.708 g; 1.5 mmol) in a yield of 30% and a purity of 91% by sublimation.

The isolated product is characterised by means of $^1H$, $^{19}F$ and $^{31}P$ NMR spectra in $CD_3CN$.

1H: 1.99 (m, 2H), 4.55 (m, 4H)
19F: −110.0 (dm, $^2J(^{19}F—^{31}P)$=87.3 Hz, 6F), −79.2 (m, 9F)
31P: −54.1 (sepm, $^2J(^{19}F—^{31}P)$=87.1 Hz, 1P)

Elemental Analysis
Experimental, %: C, 23.39; H, 1.31;
calculated for $C_9H_6F_{15}O_2P$, %: C, 23.29; H, 1.34

The invention claimed is:

1. A process for preparing a phosphinic acid ester of formula (I)

$$(C_nF_{2n+1-y}H_y)_2P(O)OR \qquad (I),$$

where n in each case, independently of one another, denotes 1, 2, 3, 4, 5, 6, 7, 8, 9, 10, 11 or 12, y in each case, independently of one another, denotes 0, 1, 2, 3 or 4, R denotes unsubstituted or substituted phenyl, a straight-chain or branched, unfluorinated or partially fluorinated or deuterated alkyl group having 1 to 30 C atoms or a straight-chain or branched, unfluorinated or partially fluorinated alkenyl or alkynyl group having 3 to 30 C atoms, where R may be partially substituted by halogen and/or partially substituted by —OH, —C(O)OH, N(CH$_3$)$_2$ and —CN and where one or two carbon atoms of the alkyl, alkenyl or alkynyl group which are not adjacent and are not in the α-position to the oxygen atom or to carbon atoms of the double bond or triple bond may be replaced by atoms and/or atom groups selected from the group consisting of —O, S, S(O)—, —SO$_2$—, —C(O)—, —C(O)O— and —N(R')— and R' in each case, independently of one another, denotes H, a straight-chain or branched, unfluorinated or partially fluorinated alkyl group having 1 to 18 C atoms, saturated C$_3$- to C$_7$-cycloalkyl, unsubstituted or substituted phenyl, comprising reacting a phosphine oxide of formula (II)

$$(C_nF_{2n+1-y}H_y)_3P(O) \tag{II},$$

where n and y have a meanings indicated for formula (I), with an alcohol or phenol R—OH in the presence of alkali-metal fluoride or tetraalkylammonium fluoride, where R has a meaning indicated for formula (I), where the water content in the reaction is in total a maximum of 1000 ppm and where alkyl in tetraalkylammonium in each case, independently of one another, denotes a straight-chain or branched alkyl group having 1 to 10 C atoms.

2. A process according to claim 1, wherein the alcohol or phenol has a residual water content between 10 to 1000 ppm.

3. A process according to claim 1, wherein the alkali-metal fluoride or tetraalkylammonium fluoride has a residual water content between 0 to 990 ppm.

4. A process according to claim 1, wherein the alkali-metal fluoride or tetraalkylammonium fluoride is added to the phosphine oxide of formula (II) at a temperature of −10° C. to 0° C., the alcohol or phenol is added, and the reaction mixture is warmed to a temperature of 20° to 60° C. until the reaction is complete.

5. A process according to claim 1, wherein no further solvent is added to the reaction.

6. A process according to claim 1, wherein y in the compounds of the formula (I) and (II) denotes 0, 1 or 2.

7. A process according to claim 1, wherein y in the compounds of the formula (I) and (II) denotes 0.

* * * * *